(12) United States Patent
Bennett et al.

(10) Patent No.: US 9,533,978 B2
(45) Date of Patent: Jan. 3, 2017

(54) PYRIMIDINE DERIVATIVES AND THEIR USE IN THE TREATMENT OF CANCER AND FURTHER DISEASES

(71) Applicant: AstraZeneca AB, Sodertalje (SE)

(72) Inventors: Nicholas James Bennett, Cheshire (GB); Stephen Thom, Cheshire (GB); Thomas McInally, Cheshire (GB)

(73) Assignee: Sumitomo Dainippon Pharma Co., Ltd, Osaka (JP)

(*) Notice: Subject to any disclaimer, the term of this patent is extended or adjusted under 35 U.S.C. 154(b) by 0 days.

(21) Appl. No.: 14/469,515

(22) Filed: Aug. 26, 2014

(65) Prior Publication Data

US 2015/0080396 A1    Mar. 19, 2015

Related U.S. Application Data

(63) Continuation of application No. 13/321,407, filed as application No. PCT/GB2010/050825 on May 20, 2010, now abandoned.

(60) Provisional application No. 61/180,238, filed on May 21, 2009.

(51) Int. Cl.
| C07D 413/12 | (2006.01) |
| C07D 239/48 | (2006.01) |
| C07D 239/49 | (2006.01) |

(52) U.S. Cl.
CPC ........... *C07D 413/12* (2013.01); *C07D 239/48* (2013.01); *C07D 239/49* (2013.01)

(58) Field of Classification Search
CPC .... C07D 413/12; C07D 239/48; C07D 239/49
See application file for complete search history.

(56) References Cited

U.S. PATENT DOCUMENTS

| 4,179,562 A | 12/1979 | Ponsford |
| 4,689,338 A | 8/1987 | Gerster |
| 4,698,348 A | 10/1987 | Gerster |
| 4,714,701 A | 12/1987 | Beauchamp |
| 4,912,112 A | 3/1990 | Seydel et al. |
| 5,736,549 A | 4/1998 | Beasley et al. |
| 5,994,361 A | 11/1999 | Penney et al. |
| 6,028,076 A | 2/2000 | Hirota et al. |
| 6,110,923 A | 8/2000 | Ely |
| 6,329,381 B1 | 12/2001 | Kurimoto et al. |
| 6,376,501 B1 | 4/2002 | Isobe et al. |
| 6,458,798 B1 | 10/2002 | Fujita et al. |
| 6,951,866 B2 | 10/2005 | Fujita et al. |
| 7,157,465 B2 | 1/2007 | Isobe et al. |
| 8,148,371 B2 | 4/2012 | Isobe et al. |
| 2003/0191086 A1 | 10/2003 | Hanus et al. |
| 2004/0214192 A1 | 10/2004 | Hashida et al. |
| 2005/0054590 A1 | 3/2005 | Averett |
| 2005/0119273 A1 | 6/2005 | Lipford et al. |
| 2007/0225303 A1 | 9/2007 | Ogita et al. |
| 2009/0118263 A1 | 5/2009 | Hashimoto et al. |
| 2009/0264447 A1 | 10/2009 | Dietz et al. |
| 2010/0099870 A1 | 4/2010 | Isobe et al. |

FOREIGN PATENT DOCUMENTS

| EP | 1 110 951 | 6/2001 |
| EP | 1 550 662 | 7/2005 |
| EP | 1 728 793 | 12/2006 |
| GB | 1375162 | 11/1974 |
| JP | 08-165292 | 6/1996 |
| JP | 11-193282 | 7/1999 |
| WO | WO 98/01448 | 1/1998 |
| WO | WO 99/28321 | 6/1999 |
| WO | WO 99/32122 | 7/1999 |
| WO | WO 99/50249 | 10/1999 |
| WO | WO 01/07027 | 2/2001 |
| WO | WO 02/04449 | 1/2002 |
| WO | WO 2004/029054 | 4/2004 |
| WO | WO 2005/009978 | 2/2005 |

(Continued)

OTHER PUBLICATIONS

Aoki, M., et al., "Weekly Dosing of AZD8848/DSP-3025, A Novel TLR7 Agonist Antedrug, Demonstrates A Prolonged Period of Control Against Markers of Pulmonary Inflammation in An Alergen Challenge Model In The Mouse", ATS New Orleans May 2010.

Balchen, T., et al., Pharmacokinetics, Safety and Tolerability of Single Ascending Intranasal Doses of AZD8848 in BChE-Deficient Volunteers. American Thoracic Society, San Francisco, May 18-23, 2012.

Bell, JP., et al., "AZD8848/DSP-3025, A Novel Potent TLR7 Agonist Antedrug, Demonstrates Negligible Systemic Activity And A Prolonged Period of Control After Cessation of Weekly Dosing in a Brown Norway Rat Ovalbumin Challenge Model", ATS New Orleans, May 2010.

(Continued)

*Primary Examiner* — James O Wilson
*Assistant Examiner* — Ebenezer O Sackey
(74) *Attorney, Agent, or Firm* — Finnegan, Henderson, Farabow, Garrett & Dunner LLP

(57) ABSTRACT

The invention concerns compounds of Formula (I): wherein $L^1$, $R^1$, $R^2$, $R^3$, $R^4$ and X are as defined in the description. The present invention also relates to processes for the preparation of such compounds, pharmaceutical compositions containing them and their use in the treatment of disease, for example cancer.

(I)

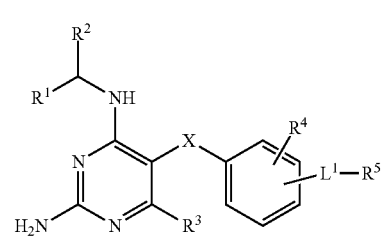

24 Claims, No Drawings

(56) References Cited

FOREIGN PATENT DOCUMENTS

| WO | WO 2006/137706 | 12/2006 |
|---|---|---|
| WO | WO 2007/031829 | 3/2007 |
| WO | WO 2008/001070 | 1/2008 |
| WO | WO 2008/015250 | 2/2008 |
| WO | WO 2008/083465 | 7/2008 |
| WO | WO 2008/114819 | 9/2008 |
| WO | WO 2009/031011 | 3/2009 |
| WO | WO 2009/067081 | 5/2009 |

OTHER PUBLICATIONS

Biffen, M., et ai , "Biological Activity of A Novel TLR7 Agonist Antedrug For The Treatment of Allergic Diseases", ATS New Orleans May 2010.
Biffen, M., et al., "Biological Characterization of a Novel Class of Toll-Like Receptor 7 Agonists Designed to Have Reduced Systematic Activity", British Journal of Pharmacology, 11(2012) pp. 573-586.
Biffen, M., et al , "Novel TLR7 Agonists for the Treatment of Allergic Diseases", Toll 2011, Riva del Garda, Italy, May 4-7, 2011.
Eiho, K., et al., "Mechanism of Long-Lasting Suppression Against TH2 Immune Response in the Lung by a Novel Antedrug TLR7 Agonist", European Respiratory Society, Amsterdam, Sep. 24-28, 2011.
English Translation of Japanese Patent Application No. 34722/1997.
English Translation of Japanese Patent Application No. 387451/1997.
Falco, E.A., et al., "2,4-Diaminopyrimidines as Antimalarials, 1, 5-Aroyloxyl and 5-Alkoxyl Derivatives", Journal of the American Chemical Society, vol. 73, No. 8 (1951) pp. 3753-3758.
Greiff, et al., "Efficacy and Tolerability of the Toll-like Receptor 7 (TLR7) Agonist AZD8848 in Patients with Seasonal Allergic Rhinitis", American Thoracic Society, San Francisco, May 18-23, 2012.
Greiff, et al., "Repeated Intranasal TLR7 Stimulation Reduces Allergen Responsiveness in Allergic Rhinitis", Respir Res., Jun. 22, 2012, 13(1):53 (27 pages).
Greiff, L., et al.,"Repeated Intranasal TLR7 Stimulation Reduces Allergen Responsiveness in Allergic Rhinitis", European Respiratory Society, Amsterdam, Sep. 24-28, 2011.
Hirota, K. et al., "Discovery of 8-Hydroxyadenines as a Novel Type of Interferon Inducer", J. Med. Chem. (2002) pp. 5419-5422.
Ikeda, K., et al., "AZD8848/DSP-3025, A Novel Potent TLR7 Agonist Antedrug, Demonstrates Efficacy Against Airway Obstruction and Other Inflammatory Endpoints in Guinea Pig Models of Rhinitis and Asthma With Acute and Weekly Dosing", ATS New Orleans May 2010.
Isobe, Y., et al., "Synthesis and Structure-Activity Relationships of 2-Substituted-8-hydroxyadenine Derivatives as Orally Available Interferon Inducers without Emetic Side Effects", Biorganic & Medicinal Chemistry 11 (2001) pp. 3641-3647.
Krueger, R.F., et al., "Tilorone Hydrochloride: An Orally Active Antiviral Agent", Science, vol. 169, Sep. 1970, pp. 1213-1215.
Kuhn, W., et al., "Impact of Dose and Dosing Frequency of Intranasal AZD8848 (a TLR7 agonist) on Biomarker Response in Healthy Volunteers", American Thoracic Society, San Francisco, May 18-23, 2012.
Kurimoto, A., et al., "Synthesis and Structure—Activity Relationships of 2-Amino-8-hydroxyadenines as Orally Active Interferon Inducing Agents", Biorganic & Medicinal Chemistry 11 (2003) pp. 5501-5508.
Kurimoto, A., et al., "Synthesis and Biological Evaluation of 8-Oxoadenine Derivatives as Toll-like Receptor 7 Agonists Introducing the Antedrug Concept," J. Med. Chem. vol. 53, No. 7 (2010) pp. 2964-2972.
Kurimoto, A., et al., "Synthesis and Biological Evaluation of Novel 9-Substituted-8-Hydroxyadenine Derivatives as Potent Interferon Inducers," Journal of Medicinal Chemistry, vol. 49, No. 6 (2006). pp. 2088-2095.
Kurimoto,A. et al., "Prodrugs of 9-Benzyl-8-hydroxy-2-(2-hydroxyethylthio)adenine: Potent Interferon Inducing Agents in Monkeys", Chem. Pharm. Bull. vol. 52, No. 4 (2004) pp. 466-469.
Kurimoto,A. et al., "Synthesis and Evaluation of 2-substituted 8-hydroxyadenines as Potent Interferon Inducers with Improved Oral Bioavailabilites". Bioorganic & Medicinal Chemistry 12 (2004) pp. 1091-1099.
Leaker, B., et al., "The Effects of the Novel Toll-like Receptor 7 (TLR7) Agonist AZD8848 on Allergen-Induced Responses in Patients with Mild Asthma", American Thoracic Society, San Francisco, May 18-23, 2012.
Leaker, B., et al., "The Effects of the Novel Toll-Like Receptor 7 (TLR7) Agonist AZD8848 on Allergen-Induced Responses in Patients with Mild Asthma", European Respiratory Society, Vienna, Sep. 1-5, 2012.
Lee, J., et al., "Molecular Basis for the Immunostimulatory Activity of Guanine Nucleoside Analogs: Activiation of Toll-like Receptor 7", Proceedings of the National Academy of Sciences USA, vol. 11, No. 100, May 27, 2003, pp. 6646-6651.
Lee, J., et al., "Activation of Anti-Hepatitis C Virus Response via Toll-like Receptor 7", Proceedings of the National Academy of Sciences USA, vol. 103, No. 6, Feb. 7, 2006. pp. 1828-1833.
Matsui, H., et al., "Mechanism of Action of Inhibition of Allergic Immune Responses by a Novel Antedrug TLR7 Agonist." The Journal of Immunology, vol. 189, No. 11, Nov. 2, 2012, pp. 5194-5205.
Matsui, H., et al., "Mechanisms of Inhibition of Type-2 Cytokines by Novel TLR7 Agonist Antedrugs", ATS New Orleans May 2010.
McInally, T. "Identification and Pharmacology of Novel TLR7 Agonist Antedrugs", RSC BMSC Inflammation Meeting, Nov. 18, 2010.
McInally, T., et al., "Indentification of a Novel TLR7 Agonist Antedrug", EFMC-ISMC 201, Brussels, Belgium, Sep. 5-9, 2010.
Nichol. F.R., "Stimulation of Murine Interferon by a Substituted Pyrimidine", Antimicrobial Agents and Chemotherapy, Mar. 1967, pp. 433-439.
Reiter, M.J., et al., "Cytokine Induction in Mice by the Immunomodulator Imiquimod", Journal of Leukocyte Biology, vol. 55, Feb. 1994, pp. 234-240.
Stringfellow, D.A., "Antiviral and Interferon-Inducing Properties of 1,5-Diamino Anthraquinones", Antimicrobial Agents and Chemotherapy, Jan. 1979, pp.111-118.
Tojo, S., et al., "Synthesis and Biological Evaluation of a Novel TLR7 Agonist with an Antedrug Strategy," EFMC-ISMC 201, Brussels Belgium, Sep. 5-9, 2010.
Yoshimoto, M., et al., "Correlation Analysis of Baker's Studies on Enzyme Inhibition, 2, Chymotrypsin, Trypsin, Thymidine Phosphorylase, uridine Phosphorylase, Thymidylate Synthetase, Cytosine Nucleoside Deaminase, Dihydrofolate Reductase, Malate Dehydrogenase, Glutarnate Dehydrogenase, Lactate Dehydrogenase, and Glyceraldehyde-phosphate Dehydrogenase", Journal of Medicinal Chemistry, vol. 19, No. 1 (1976) pp. 71-98.
International Search Report for PCT/GB2010/050825, dated Aug. 6, 2010.
Communication dated Apr. 8, 2014, from the European Patent Office regarding European Patent Application 10 721195.5 (4 pages).
International Preliminary Report on Patentability for PCT/GB2010/050825, dated Nov. 22, 2011 (7 pages).

PYRIMIDINE DERIVATIVES AND THEIR USE IN THE TREATMENT OF CANCER AND FURTHER DISEASES

CROSS REFERENCE TO RELATED APPLICATIONS

This application is a continuation application of application Ser. No. 13/321,407, filed on Feb. 1, 2012, now abandoned, which is a national phase application based on PCT/GB2010/050825, filed May 20, 2010, which claims the benefit of U.S. Provisional Application No. 61/180,238, filed May 21, 2009, all of which are incorporated herein by reference.

JOINT RESEARCH AGREEMENT

The subject matter claimed in this application was made as a result of activities undertaken within the scope of a joint research agreement between AstraZeneca AB and Sumitomo Pharmaceuticals Co. Ltd. dated Dec. 19, 2003. All of the rights and obligations of Sumitomo Pharmaceuticals Co. Ltd. were assumed by Dainippon Sumitomo Pharmaceuticals Co. Ltd., a company created by the merger of Dainippon Pharmaceutical Co. Ltd. and Sumitomo Pharmaceuticals Co. Ltd., effective Oct. 3, 2005.

FIELD OF THE INVENTION

The present invention relates to novel pyrimidine derivatives and, more particularly, to novel pyrimidine derivatives that act as TLR7 agonists. This invention also relates to methods for the preparation of such pyrimidine derivatives and novel intermediates in the preparation thereof, to pharmaceutical compositions containing such pyrimidine derivates, to the use of such pyrimidine derivatives in the preparation of medicaments, and to the use of such pyrimidine derivatives in the treatment of conditions mediated by TLR7, such as allergic diseases, autoimmune diseases, viral diseases and, in particular, cancer.

BACKGROUND OF THE INVENTION

Toll-like receptors (TLRs) are expressed on a variety of immune cells, including macrophages and dendritic cells (DCs). TLRs recognise molecular motifs on pathogens called pathogen-associated molecular patterns (PAMPs) (1). To date, 13 TLRs have been identified in man, these include TLRs 1, 2, 4, 5 and 6, which are confined to the cell surface and TLRs 3, 7, 8 and 9 which are expressed in endosomes. Different TLRs recognise different pathogen-derived ligands, for example TLRs 2 (bacterial lipoproteins), 3 (double-stranded RNA/poly (I:C)), 4 (lipopolysaccharides), 5 (flagellin), 7 (single-stranded RNA) and 9 (CpG-containing DNA) (2). Ligation of TLRs on antigen-presenting cells, such as DCs, leads to production of proinflammatory cytokines, DC maturation and priming of the adaptive immune system (3). TLR7 and TLR9 are expressed by plasmacytoid dendritic cells (pDCs) and ligand recognition leads to the secretion of interferon-α (INF-α) (4). Preclinical studies investigating the effects of activation of TLRs, using bacterial or viral components, dosed as monotherapy and/or combined with anti-tumor agents, have shown tumour growth inhibition in a variety of murine tumour models (5).

Several small molecule TLR7 agonists have been described, including the imidazoquinoline, imiquimod, which has been used to treat a number of dermatological conditions e.g. genital warts, molluscum contagiosum and melanoma. In the case of melanoma, topically applied imiquimod (Aldara, Graceway Pharmaceuticals, Bristol, Tenn.) demonstrated therapeutic responses in cutaneous metastatic melanoma and lentigo maligna (6) and has been approved for the treatment of superficial basal cell carcinoma (BCC) (7). Preclinical and clinical studies indicate that imiquimod is likely to function through the induction of type 1 IFN and IFN-inducible genes, which in turn can have direct effects on tumour cell growth and/or harness components of the adaptive immune system (6, 7). 852A is another imidazoquinoline, which unlike imiquimod, is suitable for systemic administration. Currently 852A is in phase II clinical trials in a number of cancer indications, including melanoma (8).

Nevertheless, there remains a need for further TLR7 agonists which are more effective in the treatment of disease, for example cancer, by reason of their superior potency and/or advantageous physical properties (for example, higher permeability, and/or lower plasma protein binding) and/or favourable toxicity profiles and/or favourable metabolic profiles in comparison with other known TLR7 agonists, for example 852A.

As now demonstrated herein, the pyrimidine derivates of the present invention are capable of activating TLR7 in vitro. As a consequence of this activity, the pyrimidine derivatives of the present invention are expected to have value in the prevention or treatment of human disease, for example cancer, either as a monotherapy or in combination with other chemotherapeutic agents or radiotherapy regimens.

SUMMARY OF THE INVENTION

According to a first aspect of the present invention, there is therefore provided a compound of Formula (I), or a pharmaceutically acceptable salt thereof:

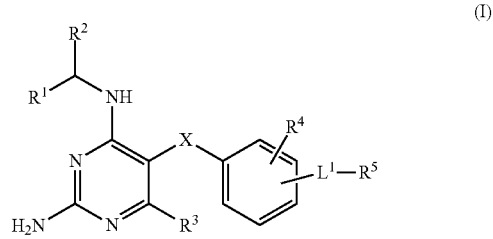

(I)

wherein:
X represents —$CH_2$—, —$NR^8$—, —O— or —$S(O)_n$—;
$R^1$ represents $C_{1-6}$alkyl, $C_{2-6}$alkoxy, $C_{1-6}$alkoxy$C_{1-6}$alkyl, hydroxy$C_{1-6}$alkyl, hydroxy$C_{1-6}$alkoxy or hydroxy$C_{1-6}$alkoxy$C_{1-6}$alkyl;
$R^2$ represents hydrogen, $C_{1-6}$alkyl or phenyl wherein said phenyl is optionally substituted with 1, 2 or 3 substituents selected from $R^6$;
$R^3$ represents $C_{1-6}$alkyl, $C_{1-6}$alkoxy or —S—$C_{1-6}$alkyl;
$R^4$ represents hydrogen, halogen, $C_{1-6}$alkyl or $C_{1-6}$alkoxy;
$L^1$ represents a direct bond, —$(CR^9R^{10})_m$—, —CH=CH—$(CR^9R^{10})_q$—, —C≡C—$(CR^9R^{10})_q$—, —O—$(CR^9R^{10})_q$—, —C(O)—O—$(CR^9R^{10})_q$— or —O—$(CH_2)_q$—$NR^8$—$(CH_2)_q$—;
$R^5$ represents methyl, hydroxy, —$NR^{11}R^{12}$, $C_{3-6}$cycloalkyl, phenyl or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from $R^7$;

$R^6$ represents $C_{1-6}$alkyl, fluoro$C_{1-6}$alkyl, $C_{1-6}$alkoxy, hydroxy, halogen, cyano, $-S(O)_n-C_{1-6}$alkyl or $-CH_2-C(O)-O-C_{1-6}$alkyl;

$R^7$ represents $C_{1-6}$alkyl, $C_{1-6}$alkoxy, $C_{1-6}$alkoxy$C_{1-6}$alkyl, hydroxy, hydroxy$C_{1-6}$alkyl or $-(CH_2)_q-NR^{11}R^{12}$;

$R^8$ represents hydrogen or $C_{1-6}$alkyl;

$R^9$ and $R^{10}$, identically or differently on each occurrence, represents hydrogen or methyl;

$R^{11}$ and $R^{12}$ independently represent hydrogen, $C_{1-4}$alkyl or $C_{1-4}$alkoxy$C_{2-4}$alkyl;

m represents 1, 2, 3, 4, 5 or 6;

n represents 0, 1 or 2; and q, independently, represents 0, 1, 2, 3, 4, 5 or 6;

with the proviso that the compound of Formula (I) is other than:

[3-(2-amino-4-methyl-6-pentylamino-pyrimidin-5-ylmethyl)]-benzoic acid ethyl ester;

[3-(2-amino-4-methyl-6-pentylamino-pyrimidin-5-ylmethyl)-phenyl]-methanol;

methyl 4-((2-amino-4-methyl-6-(pentylamino)pyrimidin-5-yl)methyl)-3-methoxybenzoate;

(4-((2-amino-4-methyl-6-(pentylamino)pyrimidin-5-yl)methyl)-3-methoxyphenyl)methanol;

methyl 4-((2-amino-4-methyl-6-(pentylamino)pyrimidin-5-yl)methyl)-3-fluorobenzoate;

(4-((2-amino-4-methyl-6-(pentylamino)pyrimidin-5-yl)methyl)-3-fluorophenyl)methanol;

or (4-((2-amino-4-methyl-6-(pentylamino)pyrimidin-5-ylmethyl)phenyl)methanol.

In one embodiment there is provided a compound of Formula (I), or a pharmaceutically acceptable salt thereof, wherein:

X represents $-CH_2-$, $-NR^8-$, $-O-$ or $-S(O)_n-$;

$R^1$ represents $C_{1-6}$alkyl, $C_{2-6}$alkoxy, $C_{1-6}$alkoxy$C_{1-6}$alkyl, hydroxy$C_{1-6}$alkyl, hydroxy$C_{1-6}$alkoxy or hydroxy$C_{1-6}$alkoxy$C_{1-6}$alkyl;

$R^2$ represents hydrogen, $C_{1-6}$alkyl or phenyl wherein said phenyl is optionally substituted with 1, 2 or 3 substituents selected from $R^6$;

$R^3$ represents $C_{1-6}$alkyl, $C_{1-6}$alkoxy or $-S-C_{1-6}$alkyl;

$R^4$ represents hydrogen, halogen, $C_{1-6}$alkyl or $C_{1-6}$alkoxy;

$L^1$ represents a direct bond, $-(CR^9R^{10})_m-$, $-CH=CH-(CR^9R^{10})_q-$, $-C\equiv C-(CR^9R^{10})_q-$, $-O-(CR^9R^{10})_q-$, $-C(O)-O-(CR^9R^{10})_q-$ or $-O-(CH_2)_q-NR^8-(CH_2)_q-$;

$R^5$ represents methyl, hydroxy, $-NR^{11}R^{12}$, $C_{3-6}$cycloalkyl, phenyl or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from $R^7$;

$R^6$ represents $C_{1-6}$alkyl, fluoro $C_{1-6}$alkyl, $C_{1-6}$alkoxy, hydroxy, halogen, cyano, $-S(O)_n-C_{1-6}$alkyl or $-CH_2-C(O)-O-C_{1-6}$alkyl;

$R^7$ represents $C_{1-6}$alkyl, $C_{1-6}$alkoxy, $C_{1-6}$alkoxy$C_{1-6}$alkyl, hydroxy, hydroxy$C_{1-6}$alkyl or $-(CH_2)_q-NR^{11}R^{12}$;

$R^8$ represents hydrogen or $C_{1-6}$alkyl;

$R^9$ and $R^{10}$, identically or differently on each occurrence, represents hydrogen or methyl;

$R^{11}$ and $R^{12}$ independently represent hydrogen, $C_{1-4}$alkyl or $C_{1-4}$alkoxy$C_{2-4}$alkyl;

m represents 1, 2, 3, 4, 5 or 6;

n represents 0, 1 or 2; and q represents 0, 1, 2, 3, 4, 5 or 6;

with the proviso that the compound of Formula (I) is other than:

[3-(2-amino-4-methyl-6-pentylamino-pyrimidin-5-ylmethyl)]-benzoic acid ethyl ester;

methyl 4-((2-amino-4-methyl-6-(pentylamino)pyrimidin-5-yl)methyl)-3-methoxybenzoate; or methyl 4-((2-amino-4-methyl-6-(pentylamino)pyrimidin-5-yl)methyl)-3-fluorobenzoate.

It is to be understood that any suitable $R^4$ and $L^1$-$R^5$ group of Formula (I) may be bonded to any available carbon atom of the phenyl ring, but not to the same carbon atom, and that $R^5$ may be linked to the phenyl ring via any suitable linker selected from $L^1$.

It is to be understood that, insofar as certain of the compounds of Formula (I) defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of Formula (I) above may exist in unsolvated forms as well as solvated forms, such as, for example, hydrated forms. It is to be understood that the present invention encompasses all such solvated forms that activate TLR7.

It is also to be understood that certain compounds of the Formula (I) may exist in crystalline form and exhibit polymorphism. The present invention encompasses all such forms that activate TLR7.

The term "halogen" or "halo" is used herein to denote fluoro, chloro, bromo and iodo.

The term "$C_{1-6}$alkyl" is intended to mean a saturated carbon chain of 1 to 6 carbon atoms in length which may be straight-chained or branched. However references to individual alkyl groups such as "propyl" are specific for the straight chain version only and references to individual branched-chain alkyl groups such as tert-butyl are specific for the branched chain version only. For example, "$C_{1-6}$alkyl" includes, but is not limited to, methyl, ethyl, propyl, isopropyl, butyl, tert-butyl, pentyl, tert-pentyl, hexyl and isohexyl. The term "$C_{1-4}$alkyl" and "$C_{1-7}$alkyl" are to be construed accordingly.

The term "$C_{3-6}$cycloalkyl" is intended to mean a saturated 3 to 6 membered monocyclic carbon ring. For example "$C_{3-6}$cycloalkyl" includes cyclopropyl, cyclobutyl, cyclopentyl and cyclohexyl.

The term "$C_{1-6}$alkoxy" is intended to mean a saturated carbon chain of 1 to 6 carbon atoms in length, which may be straight-chained or branched, linked to oxygen. For example, "$C_{1-6}$alkoxy" includes, but is not limited to, methoxy, ethoxy, propoxy, butoxy, pentoxy and hexoxy.

The term "$C_{1-6}$alkoxy$C_{1-6}$alkyl" is intended to mean a saturated carbon chain of 1 to 6 carbon atoms in length, which may be straight-chained or branched, linked via oxygen to another saturated carbon chain of 1 to 6 carbon atoms in length, which may be straight-chained or branched. For example, "$C_{1-6}$alkoxy$C_{1-6}$alkyl" includes, but is not limited to, methoxyethyl, methoxypropyl, ethoxypropyl, propoxyethyl and butoxypropyl. The term "$C_{1-4}$alkoxy$C_{2-4}$alkyl" is to be construed accordingly.

The term "hydroxy$C_{1-6}$alkyl" is intended to mean a saturated carbon chain of 1 to 6 carbon atoms in length, which may be straight-chained or branched, wherein one of the hydrogen atoms has been replaced by a hydroxy group. For example "hydroxyC$_{1-6}$alkyl" includes, but is not limited to, hydroxymethyl, hydroxyethyl, 2-hydroxypropyl, 3-hydroxypropyl, 1-hydroxyisopropyl, 4-hydroxybutyl, hydroxypentyl, hydroxyhexyl and hydroxyisohexyl.

The term "hydroxyC$_{1-6}$alkoxy" is intended to mean a saturated carbon chain of 1 to 6 carbon atoms in length, which may be straight-chained or branched, linked to oxygen and wherein one of the hydrogen atoms has been replaced by a hydroxy group. For example "hydroxyC$_{1-6}$alkoxy" includes, but is not limited to, hydroxymethoxy, hydroxyethoxy, 2-hydroxypropoxy, 3-hydroxypropoxy, 1-hydroxyisopropoxy, 4-hydroxybutoxy, hydroxypentoxy and hydroxyhexoxy.

The term "hydroxyC$_{1-6}$alkoxyC$_{1-6}$alkyl" is intended to mean a saturated carbon chain of 1 to 6 carbon atoms in length, which may be straight-chained or branched, linked via oxygen to another saturated carbon chain of 1 to 6 carbon atoms in length, which may be straight-chained or branched, and wherein one of the hydrogen atoms of one, but not both, of the carbon chains has been replaced by a hydroxy group. For example "hydroxyC$_{1-6}$alkoxyC$_{1-6}$alkyl" includes, but is not limited to, hydroxymethoxymethyl, hydroxyethoxymethyl, 2-hydroxypropoxyethyl, 3-hydroxypropoxyethyl, 1-hydroxyisopropoxyethyl, 4-hydroxybutoxypentyl, hydroxypentoxyethyl and hydroxyhexoxyethyl.

The term "aryl" is intended to mean phenyl or naphthyl.

Unless stated otherwise, the term "heterocyclic ring" is intended to mean a 4, 5, 6 or 7 membered fully saturated or partially saturated monocyclic ring which comprises 1, 2 or 3 heteroatoms selected from nitrogen, oxygen or sulphur linked via ring carbon atoms or ring nitrogen atoms. Examples of 4, 5, 6 or 7 membered heterocyclic rings include, but are not limited to, azetidinyl, tetrahydrofuranyl, dihydropyranyl, tetrahydropyranyl, pyrrolinyl, pyrrolidinyl, thiazolidinyl, morpholinyl, oxetanyl, piperidinyl, piperazinyl, dihydropyridinyl, dihydropyrimidinyl, azepanyl and diazepanyl. This definition further comprises sulphur-containing rings wherein the sulphur atom has been oxidised to an S(O) or S(O$_2$) group.

In further embodiments of the first aspect of the present invention, each of the following definitions of L$^1$, R$^1$, R$^2$, R$^3$, R$^4$, R$^5$, R$^6$, R$^7$, R$^8$, R$^9$R$^{10}$, R$^{11}$, R$^{12}$, X, and q in paragraphs (1) to (61) hereinafter may be used individually or in combination with one or more of the other following definitions to limit the broadest definition of Formula (I). For example, the skilled person would understand that paragraphs (24), (26), (34), (42) and (58) could be combined to provided a compound of Formula (I), or a pharmaceutically acceptable salt thereof, wherein R$^4$ represents C$_{1-6}$alkoxy, L$^1$ represents —O—(CR$^9$R$^{10}$)$_q$— and is bonded at the para position of the phenyl ring relative to linkage —X—, q represents 1, 2 or 3 and R$^5$ represents NR$^{11}$R$^{12}$ wherein R$^{11}$ and R$^{12}$ both represent methyl. Or, for example, the skilled person would understand that paragraphs (36), (51) and (61) could be combined to provided a compound of Formula (I), or a pharmaceutically acceptable salt thereof, wherein L$^1$ represents —C(O)—O—(CR$^9$R$^{10}$)$_q$—, q represents 0 and R$^5$ represents methyl.

(1) X represents —CH$_2$—;
(2) X represents —NR$^8$—;
(3) X represents —O—;
(4) X represents —S(O)$_n$—;
(5) R$^1$ represents C$_{1-6}$alkyl, C$_{2-6}$alkoxy, C$_{1-6}$alkoxyC$_{1-6}$alkyl, hydroxyC$_{1-6}$alkyl, hydroxyC$_{1-6}$alkoxy;
(6) R$^1$ represents C$_{1-6}$alkyl or hydroxyC$_{1-6}$alkyl
(7) R$^1$ represents C$_{1-6}$alkyl;
(8) R$^1$ represents butyl;
(9) R$^2$ represents hydrogen or C$_{1-6}$alkyl;
(10) R$^2$ represents hydrogen;
(11) R$^2$ represents C$_{1-6}$alkyl;
(12) R$^2$ represents phenyl wherein said phenyl is optionally substituted with 1, 2 or 3 substituents selected from R$^6$;
(13) R$^2$ represents phenyl wherein said phenyl is optionally substituted with 1, 2 or 3 substituents selected from halogen or fluoroC$_{1-6}$alkyl;
(14) R$^2$ represents phenyl wherein said phenyl is optionally substituted with a single substituent selected from —CH$_2$—C(O)—O—C$_{1-6}$alkyl;
(15) R$^2$ represents phenyl wherein said phenyl is optionally substituted with a single substituent selected from —CH$_2$—C(O)—O—CH$_3$ or —CH$_2$—C(O)—O—CH$_2$—CH$_3$;
(16) R$^3$ represents C$_{1-6}$alkyl;
(17) R$^3$ represents methyl;
(18) R$^3$ represents C$_{1-6}$alkoxy;
(19) R$^3$ represents —S—C$_{1-6}$alkyl;
(20) R$^4$ is bonded at the ortho position of the phenyl ring relative to linkage —X—;
(21) R$^4$ represents hydrogen, fluorine, methyl or C$_{1-6}$alkoxy
(22) R$^4$ represents hydrogen or C$_{1-6}$alkoxy;
(23) R$^4$ represents hydrogen;
(24) R$^4$ represents C$_{1-6}$alkoxy;
(25) R$^4$ represents methoxy;
(26) L$^1$ is bonded at the para position of the phenyl ring relative to linkage —X—;
(27) L$^1$ is bonded at the meta position of the phenyl ring relative to linkage —X—;
(28) L$^1$ is bonded at the ortho position of the phenyl ring relative to linkage —X—;
(29) L$^1$ represents —(CR$^9$R$^{10}$)$_m$—, —CH=CH—(CR$^9$R$^{10}$)$_q$— or —C≡C—(CR$^9$R$^{10}$)$_q$—;
(30) L$^1$ represents —O—(CR$^9$R$^{10}$)$_q$— or —C(O)—O—(CR$^9$R$^{10}$)$_q$—;
(31) L$^1$ represents —O—(CH$_2$)$_q$—NR$^8$—(CH$_2$)$_q$—;
(32) L$^1$ represents —O—(CR$^9$R$^{10}$)$_q$— or —C(O)—O—(CR$^9$R$^{10}$)$_q$— wherein q represents 1, 2, 3, 4 or 5 and R$^5$ represents —NR$^{11}$R$^{12}$ or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from R$^7$;
(33) L$^1$ represents —O—(CR$^9$R$^{10}$)$_q$— or —C(O)—O—(CR$^9$R$^{10}$)$_q$— wherein R$^9$ and R$^{10}$ both represent hydrogen, q represents 1, 2, 3, 4 or 5 and R$^5$ represents —NR$^{11}$R$^{12}$ or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from R$^7$;
(34) L$^1$ represents —O—(CR$^9$R$^{10}$)$_q$—;
(35) L$^1$ represents —O—(CR$^9$R$^{10}$)$_q$— wherein R$^9$ and R$^{10}$ both represent hydrogen;
(36) L$^1$ represents —C(O)—O—(CR$^9$R$^{10}$)$_q$—;
(37) L$^1$ represents a direct bond;
(38) R$^5$ represents hydroxy, —NR$^{11}$R$^{12}$, C$_{3-6}$cycloalkyl, phenyl or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from $R^7$;
(39) $R^5$ represents $-NR^{11}R^{12}$, $C_{3-6}$cycloalkyl, phenyl or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from $R^7$;
(40) $R^5$ represents $NR^{11}$, $R^{12}$ or a monocyclic 4, 5, 6 or 7 membered heterocyclic ring which comprises 1, 2 or 3 heteroatoms independently selected from O, N or S wherein said heterocyclic ring is optionally substituted with 1, 2 or 3 substituents selected from $R^7$;
(41) $R^5$ represents $NR^{11}R^{12}$;
(42) $R^5$ represents $NR^{11}R^{12}$ wherein $R^{11}$ and $R^{12}$ both represent methyl;
(43) $R^5$ represents a monocyclic 4, 5, 6 or 7 membered heterocyclic ring which comprises 1, 2 or 3 heteroatoms independently selected from O, N or S wherein said heterocyclic ring is optionally substituted with 1, 2 or 3 substituents selected from $R^7$;
(44) $R^5$ represents a nitrogen-linked monocyclic 4, 5, 6 or 7 membered heterocyclic ring which optionally comprises, in addition to the nitrogen atom via which the heterocyclic ring is linked to $L^1$, 1 or 2 further heteroatoms independently selected from O, N or S wherein said heterocyclic ring is optionally substituted with 1, 2 or 3 substituents selected from $R^7$;
(45) $R^5$ represents piperazinyl, piperidinyl or pyrrolidinyl wherein said piperazinyl, piperidinyl or pyrrolidinyl ring is optionally substituted with 1, 2 or 3 substituents selected from $R^7$;
(46) $R^5$ represents piperazin-1-yl, piperidin-1-yl or pyrrolidin-1-yl wherein said piperazin-1-yl, piperidin-1-yl or pyrrolidin-1-yl ring is optionally substituted with 1, 2 or 3 substituents selected from $R^7$;
(47) $R^5$ represents piperazinyl, piperidinyl or pyrrolidinyl wherein said piperazinyl, piperidinyl or pyrrolidinyl ring is optionally substituted with a single methyl substituent;
(48) $R^5$ represents piperazin-1-yl, piperidin-1-yl or pyrrolidin-1-yl wherein said piperazin-1-yl, piperidin-1-yl or pyrrolidin-1-yl ring is optionally substituted with a single methyl substituent;
(49) $R^5$ represents an unsubstituted piperazinyl, piperidinyl or pyrrolidinyl ring;
(50) $R^5$ represents phenyl;
(51) $R^5$ represents methyl;
(52) $R^5$ represents hydroxy
(53) $R^8$ represents hydrogen or methyl;
(54) $R^8$ represents hydrogen;
(55) $R^8$ represents methyl;
(56) q represents 1, 2, 3, 4, 5 or 6;
(57) q represents 1, 2, 3 or 4;
(58) q represents 1, 2 or 3;
(59) q represents 2 or 3;
(60) q represents 3;
(61) q represents 0.

Particular novel compounds of Formula (I) include, but are not limited to, the following compounds:
5-(4-methoxybenzyl)-6-methyl-$N^4$-pentylpyrimidine-2,4-diamine;
4-amino-4-methyl-6-pentylamino-pyrimidin-5-ylmethyl)-phenol;
5-(4-(2-(dimethylamino)ethoxy)benzyl)-6-methyl-$N^4$-pentylpyrimidine-2,4-diamine;
5-(4-(3-(dimethylamino)propoxy)benzyl)-6-methyl-$N^4$-pentylpyrimidine-2,4-diamine;
6-methyl-$N^4$-pentyl-5-(4-(2-(piperidin-1-yl)ethoxy)benzyl)pyrimidine-2,4-diamine;
6-methyl-$N^4$-pentyl-5-(4-(2-(pyrrolidin-1-yl)ethoxy)benzyl)pyrimidine-2,4-diamine;
5-(4-(2-(benzyl(methyl)amino)ethoxy)benzyl)-6-methyl-$N^4$-pentylpyrimidine-2,4-diamine;
3-(4-((2-amino-4-methyl-6-(pentylamino)pyrimidin-5-yl)methyl)phenoxy)propan-1-ol;
6-methyl-$N^4$-pentyl-5-(4-(3-(pyrrolidin-1-yl)propoxy)benzyl)pyrimidine-2,4-diamine;
6-methyl-5-(4-(3-(4-methylpiperazin-1-yl)propoxy)benzyl)-$N^4$-pentylpyrimidine-2,4-diamine;
5-(4-(3-(dimethylamino)propoxy)-2-methoxybenzyl)-6-methyl-$N^4$-pentylpyrimidine-2,4-diamine;
methyl 4-((2-amino-4-methyl-6-(pentylamino)pyrimidin-5-yl)methyl)-3-methoxybenzoate;
(S)-methyl 4-((2-amino-4-(1-hydroxypentan-2-ylamino)-6-methylpyrimidin-5-yl)methyl)-3-methoxybenzoate;
(S)-methyl 4-((2-amino-4-(1-hydroxyheptan-3-ylamino)-6-methylpyrimidin-5-yl)methyl)-3-methoxybenzoate;
(S)-4-(dimethylamino)butyl 4-((2-amino-4-(1-hydroxypentan-2-ylamino)-6-methylpyrimidin-5-yl)methyl)-3-methoxybenzoate benzene sulphonate;
methyl 3-((2-amino-4-methyl-6-(pentylamino)pyrimidin-5-yl)methyl)-4-methoxybenzoate;
methyl 3-((2-amino-4-methyl-6-(pentylamino)pyrimidin-5-yl)methyl)-4-fluorobenzoate;
methyl 4-((2-amino-4-methyl-6-(pentylamino)pyrimidin-5-yl)methyl)-3-fluorobenzoate;
5-(2-methoxybenzyl)-6-methyl-$N^4$-pentylpyrimidine-2,4-diamine;
2-((2-amino-4-methyl-6-(pentylamino)pyrimidin-5-yl)methyl)phenol;
5-(2-ethoxybenzyl)-6-methyl-$N^4$-pentylpyrimidine-2,4-diamine;
5-(2-(3-(dimethylamino)propoxy)benzyl)-6-methyl-$N^4$-pentylpyrimidine-2,4-diamine;
5-(3-methoxybenzyl)-6-methyl-$N^4$-pentylpyrimidine-2,4-diamine;
3-((2-amino-4-methyl-6-(pentylamino)pyrimidin-5-yl)methyl)phenol;
5-(3-(3-(dimethylamino)propoxy)benzyl)-6-methyl-$N^4$-pentylpyrimidine-2,4-diamine;
6-methyl-$N^4$-pentyl-5-(3-(2-(piperidin-1-yl)ethoxy)benzyl)pyrimidine-2,4-diamine;
5-(3-(2-(dimethylamino)ethoxy)benzyl)-6-methyl-$N^4$-pentylpyrimidine-2,4-diamine;
6-methyl-$N^4$-pentyl-5-(3-(2-(pyrrolidin-1-yl)ethoxy)benzyl)pyrimidine-2,4-diamine;
5-(3-((dimethylamino)methyl)benzyl)-6-methyl-$N^4$-pentylpyrimidine-2,4-diamine;
5-(4-(3-(dimethylamino)prop-1-ynyl)benzyl)-6-methyl-$N^4$-pentylpyrimidine-2,4-diamine;
5-(4-(3-(dimethylamino)propyl)benzyl)-6-methyl-$N^4$-pentylpyrimidine-2,4-diamine;
5-(3-(3-(dimethylamino)propyl)benzyl)-6-methyl-$N^4$-pentylpyrimidine-2,4-diamine;
5-(4-(3-(dimethylamino)propoxy)-2-methylbenzyl)-6-methyl-$N^4$-pentylpyrimidine-2,4-diamine;
(R)-methyl 2-(3-(1-(2-amino-5-(4-(3-(dimethylamino)propoxy)benzyl)-6-methylpyrimidin-4-ylamino)-3-hydroxypropyl)phenyl)acetate;
(R)-methyl 2-(3-(1-(2-amino-5-(4-(3-(dimethylamino)propoxy)-2-methoxybenzyl)-6-methylpyrimidin-4-ylamino)-3-hydroxypropyl)phenyl)acetate;
and pharmaceutically acceptable salts thereof.

In one embodiment there is provided (S)-4-(dimethylamino)butyl 4-((2-amino-4-(1-hydroxypentan-2-ylamino)-6-methylpyrimidin-5-yl)methyl)-3-methoxybenzoate.

In a further embodiment there are provided compounds of Formula (I) selected from:

3-(4-((2-amino-4-methyl-6-(pentylamino)pyrimidin-5-yl)methyl)-3-methoxyphenoxy)propan-1-ol;

5-(2-methoxy-4-(3-morpholinopropoxy)benzyl)-6-methyl-N$^4$-pentylpyrimidine-2,4-diamine;

5-(2-methoxy-4-(3-(4-methylpiperazin-1-yl)propoxy) benzyl)-6-methyl-N$^4$-pentylpyrimidine-2,4-diamine;

5-(4-(4-(dimethylamino)butyl)-2-methoxybenzyl)-6-methyl-N4-pentylpyrimidine-2,4-diamine; and (S)-2-(2-amino-5-(4-(hydroxymethyl)-2-methoxybenzyl)-6-methylpyrimidin-4-ylamino)pentan-1-ol;

and pharmaceutically acceptable salts thereof.

In one embodiment of the invention there is provided any Example described herein, or a pharmaceutically acceptable salt thereof.

A suitable pharmaceutically-acceptable salt of a compound of the Formula (I) is, for example, an acid-addition salt of a compound of the Formula (I), for example an acid-addition salt with an inorganic or organic acid such as hydrochloric, hydrobromic, sulphuric, trifluoroacetic, citric or maleic acid.

The compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in-vivo cleavable amide derivatives that may be formed at an amino group in a compound of the Formula (I).

Accordingly, the present invention includes those compounds of the Formula (I) as defined hereinbefore when made available by organic synthesis and when made available within the human or animal body by way of cleavage of a pro-drug thereof. Accordingly, the present invention includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically-acceptable pro-drug of a compound of the Formula (I) is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses an amino group is, for example, an in-vivo cleavable amide derivative thereof. Suitable pharmaceutically-acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in-vivo effects of a compound of the Formula (I) may be exerted in part by one or more metabolites that are formed within the human or animal body after administration of a compound of the Formula (I). As stated hereinbefore, the in-vivo effects of a compound of the Formula (I) may also be exerted by way of metabolism of a precursor compound (a pro-drug).

Preparation of Compounds of Formula (I)

Certain processes for the synthesis of compounds of Formula (I) are provided as a further feature of the invention. Thus, according to a further aspect of the invention there is provided a process for the preparation of a compound of Formula (I) or a pharmaceutically acceptable salt thereof, which comprises a process (a), (b), (c) or (d) wherein, unless otherwise defined, the variables are as defined hereinbefore for compounds of Formula (I):

(a) when $R^3$ represents $C_{1-6}$alkyl and $L^1$ represents —O—$(CR^9R^{10})_q$—, reaction of a compound of Formula (IX) with a group halo-$(CR^9R^{10})_q$—$R^5$;

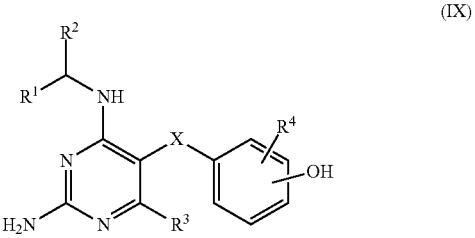

(b) when $L^1$ represents —C(O)—O—$(CR^9R^{10})_q$— and $R^5$ represents $NR^{11}R^{12}$, reaction of an acid of Formula (XVI) with an alcohol of formula OH—$(CR^9R^{10})_q$—$NR^{11}R^{12}$ in the presence oxalyl chloride or thionyl chloride, a suitable coupling agent and optionally a suitable base;

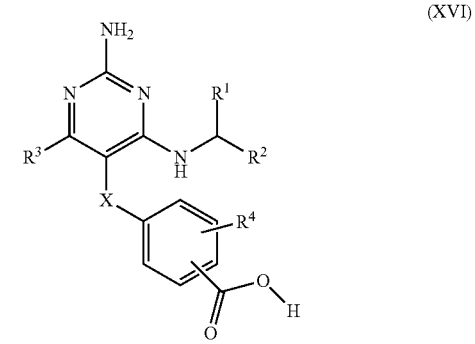

(c) when $L^1$ represents —$(CR^9R^{10})_m$-(and m represents 2, 3, 4, 5 or 6), —CH═CH—$(CR^9R^{10})_q$— or —C≡C—

$(CR^9R^{10})_q$—, reaction of a compound of Formula (XVII) with a compound of Formula (XVIII) in the presence of copper iodide, a suitable catalyst and a suitable base;

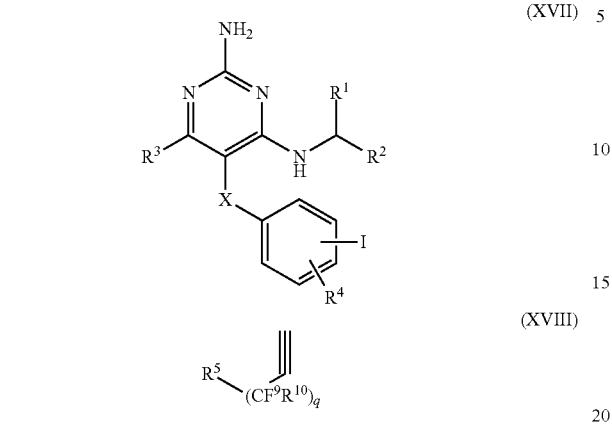

(XVII)

(XVIII)

(d) when $R^3$ represents $C_{1-6}$alkoxy or —S—$C_{1-6}$alkyl, reaction of a compound of Formula (XXXIII) with the appropriate alcohol or alkylthiol in the presence of a suitable base;

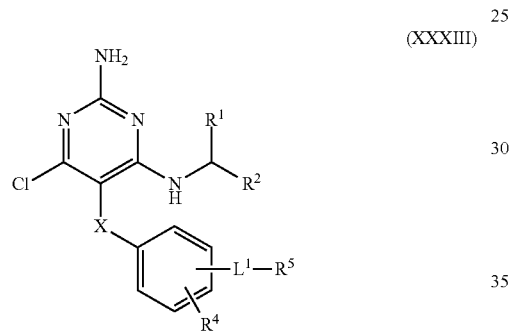

(XXXIII)

and thereafter, if necessary:
(i) converting a compound of Formula (I) into another compound of Formula (I);
(ii) removing any protecting groups;
(iii) separating a racemic mixture into separate enantiomers;
(iv) preparing a pharmaceutically acceptable salt thereof; and/or
(v) preparing a crystalline form thereof.

Compounds of Formula (Ia) in which X represents $CH_2$, $R^3$ represents $C_{1-6}$alkyl, $L^1$ represents —O—$(CR^9R^{10})_q$—, Et represents an ethyl group, $R^4$ is other than $C_{1-6}$alkoxy and all other variables are as defined hereinbefore for compounds of Formula (I), may be prepared as described in the following reaction Scheme 1.

Scheme 1

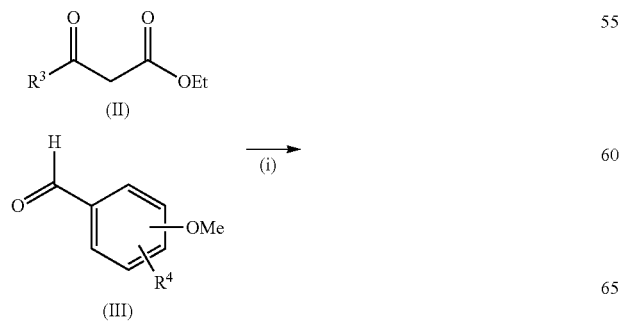

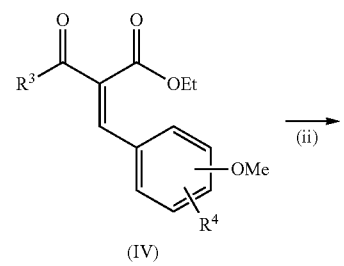

(IV)

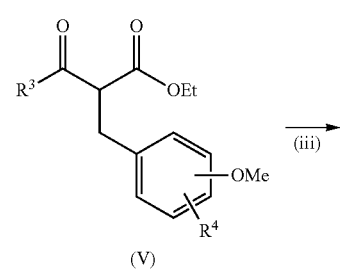

(V)

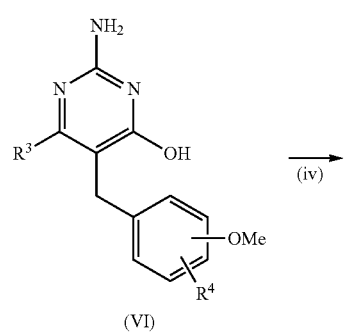

(VI)

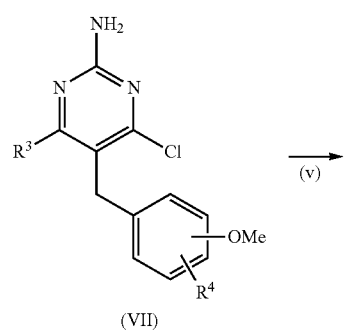

(VII)

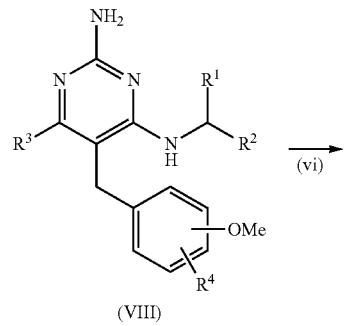

(VIII)

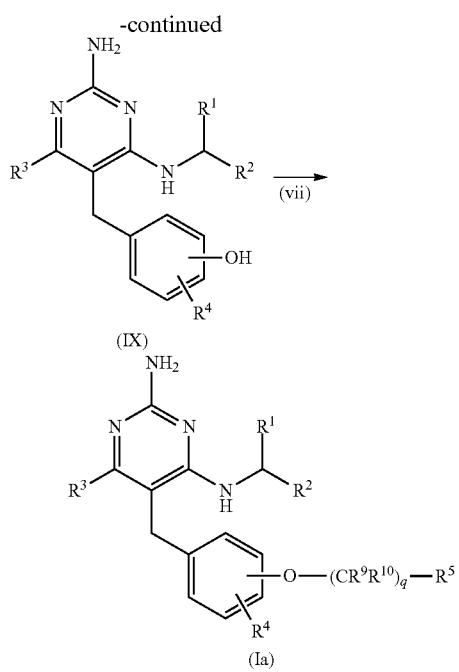

Step (i)—A compound of Formula (IV) can be prepared by reaction of a compound of Formula (III) with a compound of Formula (II). The reaction may be carried out in the presence of acetic acid and piperidine in a suitable solvent, such as toluene, and at a suitable temperature, for example 50° C. to 150° C.

Step (ii)—Compounds of Formula (V) can be prepared by reduction of a compound of Formula (IV). The reaction may be carried out with a catalyst such as Pd/C under a $H_2$ atmosphere (1-20 bar) in a suitable solvent, such as EtOH, and at a suitable temperature, for example 20° C. to 100° C.

Step (iii)—Compounds of Formula (VI) may be prepared by reacting a compound of Formula (V) with guanidine or guanidine carbonate in a suitable solvent, such as MeOH or EtOH, and at a suitable temperature, for example 50° C. to 150° C.

Step (iv)—Compounds of Formula (VII) may be prepared by reacting a compound of Formula (VI) with phosphorous oxychloride, at a suitable temperature, for example 50° C. to 110° C.

Step (v)—Compounds of Formula (VIII) may be prepared by reacting a compound of Formula (VII) with an excess of amine of formula $NH_2CHR^1R^2$ in a suitable solvent, such as butanol or 1,4-dioxane, at a suitable temperature, for example 50° C. to 150° C. Alternatively, the reaction may be performed in a microwave at a suitable temperature, for example 50° C. to 200° C.

Step (vi)—Compounds of Formula (IX) may be prepared by reacting a compound of Formula (VIII) with a solution of $BBr_3$ in a suitable solvent, such as DCM, and at a suitable temperature, for example 0° C. to 15° C.

Step (vii)—compounds of Formula (IX) may be reacted with a group halo-$R^5$ or halo-$(CR^9R^{10})_q$—$R^5$ in the presence of a suitable base, for example $Cs_2CO_3$, in a suitable solvent, for example NMP or DMF, optionally in the presence of NaI and at a suitable temperature, for example 50° C. to 150° C., to provide a compound of Formula (Ia).

Alternatively, compounds of Formula (VIII) may be prepared by reacting a compound of Formula (X), in which $R^{13}$ represents an aryl group, with excess of amine of formula $NH_2CHR^1R^2$. The reaction may be carried out in a suitable solvent, such as butanol or 1,4-dioxane, and at a suitable temperature, for example 50° C. to 150° C. Alternatively, the reaction may be performed in a microwave at a suitable temperature, for example 50° C. to 200° C.

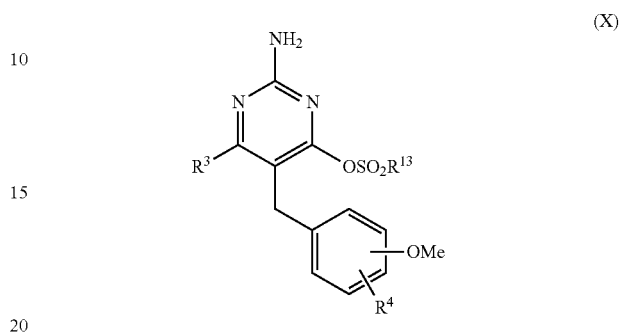

A compound of Formula (X) may be prepared by reacting a compound of Formula (VI) with an aryl sulphonylchloride of formula $R^{13}SO_2Cl$. The reaction may be carried out in a suitable solvent, such as DCM, in the presence of a suitable base, such as triethylamine or DIPEA, and with the addition of a catalyst, such as DMAP, at a suitable temperature, for example 0° C. to 50° C.

Alternatively compounds of Formula (V) may be prepared as shown in Scheme 2 by reacting a compound of Formula (III) with a base, such as NaH, in a suitable solvent, such as THF or DMF, at a suitable temperature, for example 0° C. to r.t. (20° C.), followed by addition of a compound of Formula (XI) wherein LG represents a suitable leaving group, for example bromine or chlorine. The reaction is then preferably heated, for example at 50° C. to 100° C., optionally in the presence of an additive such as KI.

Scheme 2

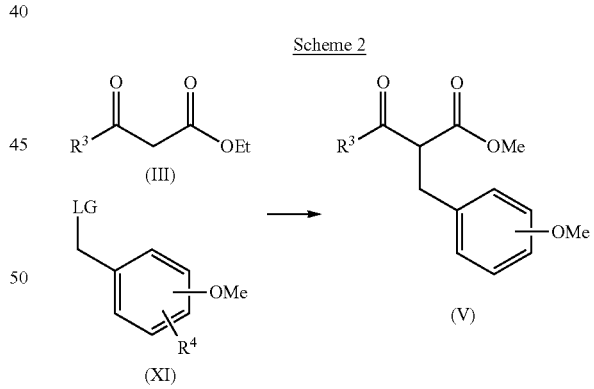

Alternatively compounds of Formula (V) may be prepared by a Heck reaction between a compound of Formula (XII) and a compound of Formula (XIII) as shown in Scheme 3 wherein Hal represents bromine or iodine. The reaction may be carried out using a palladium catalyst, such as $Pd(OAc)_2$ or 1,1'-bis(di-tert-butylphosphino)ferrocene-palladium(II) chloride (Pd-118), a base such as $NaHCO_3$ or dicyclohexylmethylamine, and tetrabutylammonium chloride or bromide. The reaction is performed in a suitable solvent, such as THF or DMA, and at a suitable temperature, for example 50° C. to 150° C.

Scheme 3

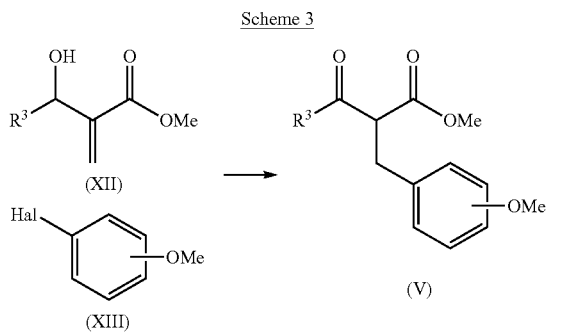

Alternatively compounds of Formula (I) wherein X represents $CH_2$, and $L^1$ represents —C(O)—O— and $R^5$ represents methyl can be prepared according to Scheme 2 from compounds of Formula (XIV) where LG represents bromo and which are either commercially available or prepared by bromination of the appropriate precursor using N-bromo-succcinimide in the presence of light and a radical initiator such as di-benzoyl peroxide or 2,2'-azobisisobutyronitrile in a suitable solvent, such as DCM, $CHCl_3$ or $CCl_4$.

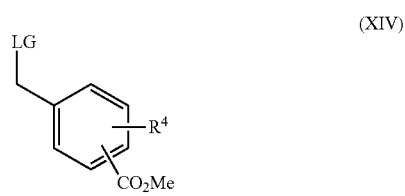

(XIV)

Compounds of Formula (Ib) wherein $L^1$ represents —C(O)—O—$(CR^9R^{10})_q$— and $R^5$ represents $NR^{11}R^{12}$ may be prepared according to Scheme 4 from compounds of type (XV) by hydrolysis of the ester in the presence of a base, such as aqueous LiOH containing an alcohol such as EtOH, and at a suitable temperature, for example 20° C. to 50° C., followed by activation of the acid of Formula (XVI), for example with $COCl_2$ or $SOCl_2$ or with a coupling agent such as O-(7-azabezotriazol-1-yl)-N,N,N',N'-tetramethyluronium hexafluorophosphate or benzotriazol-1-yloxytripyrrolidino-phosphonium hexafluoro-phosphate, and reaction with a suitable alcohol group containing $NR^{11}R^{12}$ in an organic solvent such as NMP, DMF, MeCN or THF and usually in the presence of a suitable base, for example triethylamine or DIPEA, and at a suitable temperature, for example 0° C. to 50° C.

Scheme 4

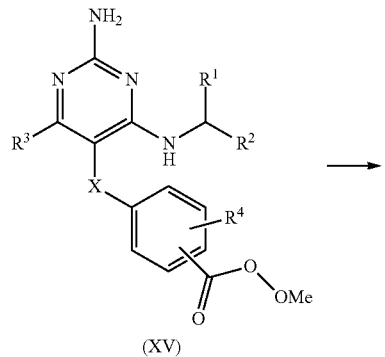

(XV)

Compounds of Formula (Ic), (Id) or (Ie) wherein $L^1$ represents —$(CR^9R^{10})_m$— (and m represents 2, 3, 4, 5 or 6), —CH=CH—$(CR^9R^{10})_q$— or —C≡C—$(CR^9R^{10})_q$— may be prepared according to Scheme 5 from compounds of Formula (XVII) by reaction with alkynes of Formula (XVIII) in the presence of CuI followed by addition of compounds of Formula (XVII) and a Pd(0) catalyst, such as $Pd(PPh_3)_4$, in a suitable solvent, such as THF, in the presence of a suitable base, such as triethylamine or DIPEA, and at a suitable temperature, e.g. 50° C.-100° C. for 6-24 hours, to give compounds of Formula (Ic). Reduction of compounds of Formula (Ic) with a catalyst, such as Pd/C, in a suitable solvent, such as EtOH under a pressure of $H_2$, e.g. 1-3 bar, provides compounds of Formula (Id). Further reduction under the same conditions provides compounds of Formula (Ie).

Scheme 5

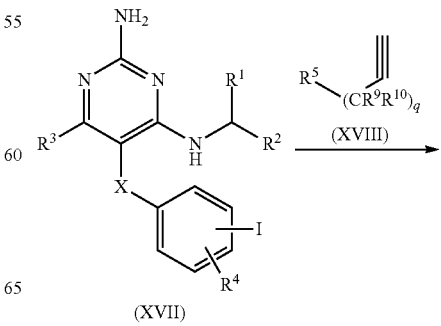

(XVII)

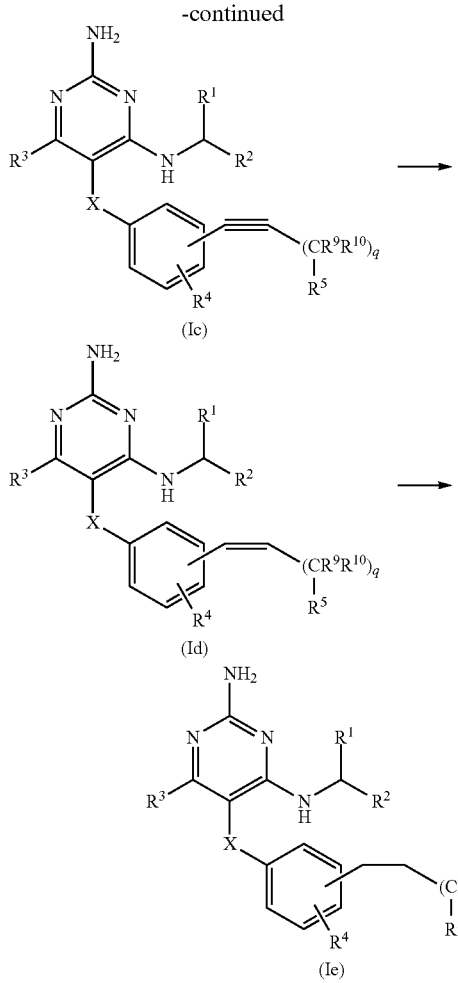

(Ic)

(Id)

(Ie)

Compounds of Formula (I) where $L^1$ represents a direct bond and $R^5$ represents a monocyclic 4, 5, 6 or 7 membered heterocyclic ring may be prepared according to Scheme 3 from compounds of Formula (XIX) and compounds of Formula (XX) and following the steps in reaction Scheme 1 from compounds of Formula (V). The reaction may be carried out using a palladium catalyst, such as palladium acetate or Pd-118, a base such as NaHCO$_3$ or dicyclohexylmethylamine, and tetrabutylammoniun chloride or bromide. The reaction is performed in a suitable solvent such as THF or DMA and at a suitable temperature, for example 50° C. to 150° C.

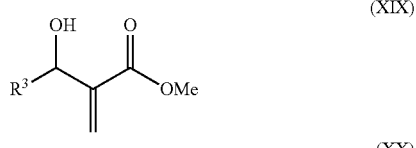

(XIX)

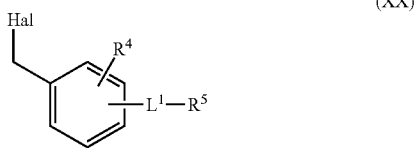

(XX)

A compound of Formula (I) in which X represents a sulphur atom may be prepared by reacting a compound of Formula (XXI) with a compound of Formula (XXII) and then by following the steps in reaction Scheme 1 from Formula (VI). The reaction may be carried out in a suitable solvent, such as ethylene glycol, and a base such as K$_2$CO$_3$, and at a suitable temperature, for example 80° C. to 200° C.

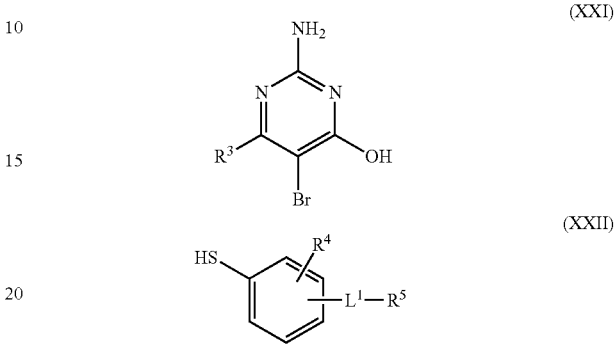

(XXI)

(XXII)

A compound of Formula (I) in which X represents an oxygen atom may be prepared by reacting a compound of Formula (XXIII), where LG represents a suitable leaving group, for example bromine, with a compound of Formula (XXIV) and then by following the steps in reaction Scheme 1 from Formula (V). The reaction may be carried out in a suitable solvent, such as THF, and in the presence of a base, such as K$_2$CO$_3$, and at a suitable temperature, for example 20° C. to 100° C.

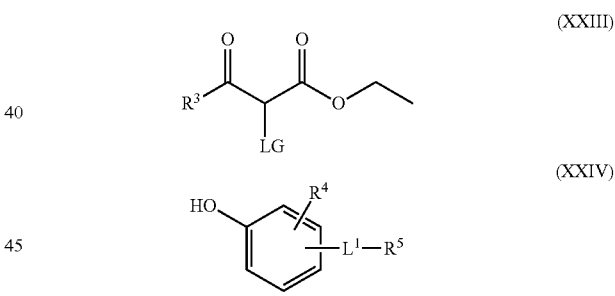

(XXIII)

(XXIV)

A compound of Formula (I) in which X represents a group NH may be prepared by reacting a compound of Formula (XXV) with a compound of Formula (XXVI) then by following the steps in reaction Scheme 1 from Formula (V). The benzyl protecting group may be removed by catalytic hydrogenation at a convenient step in the route. The reaction may be carried out in a suitable solvent, such as toluene, and with a suitable catalyst, such as rhodium acetate, and at a suitable temperature, for example 50° C. to 150° C.

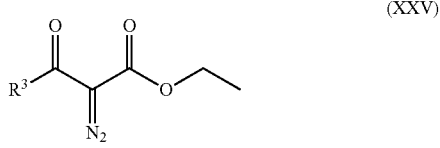

(XXV)

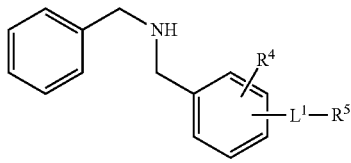
(XXVI)

A compound of Formula (I) in which X represents a group NR$^8$, wherein R$^8$ is C$_{1-6}$alkyl, may be prepared by reacting a compound of Formula (XXV) with a compound of Formula (XXVII) then by following the steps in reaction Scheme 1 from Formula (V).

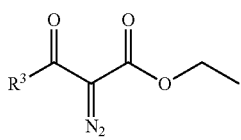
(XXV)

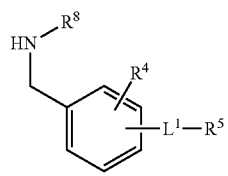
(XXVII)

A compound of Formula (I) in which R$^3$ represents a group C$_{1-6}$alkoxy or —S—C$_{1-6}$alkyl may be prepared according to Scheme 6.

Scheme 6

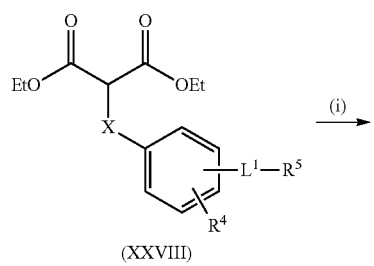
(XXVIII)

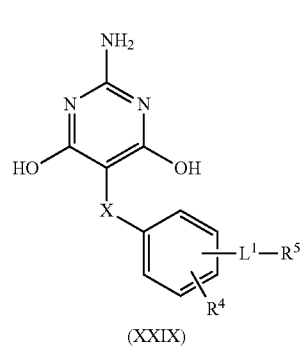
(XXIX)

(XXX)

(XXXI)

(I)

Step (i)—Compounds of Formula (XXIX) may be prepared by reacting a compound of Formula (XXVIII) with guanidine or guanidine carbonate in a suitable solvent, such as MeOH or EtOH, and at a suitable temperature, for example 50° C.-150° C.

Step (ii)—Compounds of Formula (XXX) may be prepared by reacting a compound of Formula (XXIX) with POCl$_3$, at a suitable temperature, for example 50° C. to 110° C.

Step (iii)—Compounds of Formula (XXXI) may be prepared by reacting a compound of Formula (XXX) with excess of an amine of Formula NH$_2$CHR$^1$R$^2$, in a suitable solvent, such as butanol or 1,4-dioxane, and at a suitable temperature, for example 50° C. to 150° C. Alternatively, the reaction can be performed in a microwave at a suitable temperature, for example 0° C. to 200° C.

Step (iv)—A compound of Formula (I) may be prepared by reacting a compound of Formula (XXXI) with the appropriate alcohol or alkylthiol in the presence of a suitable base, such as NaH.

Biological Assays

The ability of compounds to activate TLR7 in vitro was assessed using the human TLR7 assay described below.

Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound ($EC_{50}$). TLR7 activity for compounds of the present invention was assessed using the human TLR7 assay and the results are shown in Table 1 below wherein the degree of TLR7 activation for each compound is expressed as a $pEC_{50}$ value.

TABLE 1

| Ex. No. | pEC50 |
|---|---|
| 1 | 5.7 |
| 2 | 5.9 |
| 3 | 7.2 |
| 4 | 7.2 |
| 5 | 6.9 |
| 6 | 7 |
| 7 | 6.2 |
| 8 | 6.3 |
| 9 | 7.2 |
| 10 | 7.1 |
| 11 | 8.6 |
| 12 | 7.2 |
| 13 | 7 |
| 14 | 8 |
| 15 | 6.9 |
| 16 | 7.3 |
| 17 | 5.5 |
| 18 | 5.7 |
| 19 | 7.2 |
| 20 | 6.9 |
| 21 | 6.5 |
| 22 | 5.9 |
| 23 | 5.6 |
| 24 | 5.3 |
| 25 | 6.1 |
| 26 | 6.2 |
| 27 | 6.4 |
| 28 | 5.9 |
| 29 | 6.5 |
| 30 | 7 |
| 31 | 7 |
| 32 | 6.6 |
| 33 | 6.6 |
| 34 | 5.7 |
| 35 | 6.5 |
| 36 | 7.3 |
| 37 | 8.1 |
| 38 | 8.2 |
| 39 | 8.4 |
| 40 | 7.7 |

According to a further aspect of the invention there is provided a pharmaceutical composition which comprises a compound of the Formula (I), or a pharmaceutically acceptable salt thereof, as defined hereinbefore in association with a pharmaceutically-acceptable diluent or carrier. The pharmaceutical composition may be used in the treatment of cancer. The composition may be in a form suitable for oral administration, for example as a tablet or capsule; for parenteral injection (including intravenous, subcutaneous, intramuscular, intravascular or infusion) as a sterile solution, suspension or emulsion; for topical administration as an ointment or cream; or for rectal administration as a suppository.

The compound of Formula (I), or a pharmaceutically acceptable salt thereof, could also be administered as an air spray for inhalation. The air spray (e.g., spray, aerosol, dry powder preparation, etc.) could be optionally formulated as an aqueous solution or suspension, or as an aerosol delivered from a pressurized pack such as a pressurised metered dose inhaler by using, for example, a liquefied propellant. A dry powder preparation may also be used. An aerosol appropriate for inhalation may be either a suspension or solution, and would typically contain the compound of Formula (I), or a pharmaceutically acceptable salt thereof, and any appropriate propellants such as a fluorocarbon or hydrogen-containing chlorofluorocarbon or a mixture thereof. Specifically, it may contain hydrofluoroalkane, particularly 1,1,1,2-tetrafluoroethane, heptafluoroalkane (HFA) such as 1,1,1,2,3,3,3-heptafluoro-n-propane, or a mixture thereof. An aerosol may optionally contain an additional preparation excipient well-known to those skilled in the art such as surfactant (e.g., oleic acid or lecithin) and cosolvent (e.g., ethanol), etc. Specifically, an aerosol preparation could be delivered using the inhaler known as "Turbuhaler™".

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compound of Formula (I) will normally be administered to a warm-blooded animal at a unit dose within the range 5-5000 mg/m² body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

In the context of the present specification, the term "therapy" also includes "prophylaxis" unless there are specific indications to the contrary. The terms "therapeutic" and "therapeutically" should be construed accordingly.

As used herein, the term "treatment" is intended to have its normal everyday meaning of dealing with a disease in order to entirely or partially relieve one, some or all of its symptoms, or to correct or compensate for the underlying pathology.

As used herein, the term "prophylaxis" is intended to have its normal everyday meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The compounds defined in the present invention are effective activators of TLR7 in vitro. Accordingly, the compounds of the present invention are expected to be potentially useful agents in the treatment of diseases or medical conditions mediated alone or in part by TLR7. For example, the following diseases and conditions listed in paragraphs 1 to 8 below may be treatable with compounds of the present invention.

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;
3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;
4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
5. allograft rejection: acute and chronic following, for example, transplantation of kidney, heart, liver, lung, bone marrow, skin or cornea or following blood transfusion; or chronic graft versus host disease;
6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and parancoplastic syndromes; and,
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as fungal diseases, chlamydia, candida, aspergillus, cryptococcal meningitis, pneumocystis carnii, cryptosporidiosis, histoplasmosis, toxoplasmosis, trypanosome infection and leishmaniasis.

It is envisaged that for the methods of treatment mentioned herein, the compound of Formula (I) will be administered to a mammal, more particularly a human being. Similarly, for the uses of a compound of Formula (I) for the treatment of diseases or medical conditions mentioned herein, it is envisaged that the compound of Formula (I) will be administered to a mammal, more particularly a human being.

According to a another aspect of the invention, there is therefore provided a compound of Formula (I) as defined hereinbefore, or a pharmaceutically acceptable salt thereof, for use as a medicament.

According to a further aspect of the invention, there is provided a compound of Formula (I) as defined hereinbefore, or a pharmaceutically acceptable salt thereof for use in the treatment of a disease mediated through TLR7. In one embodiment of the invention, said disease mediated through TLR7 is cancer. In a further embodiment of the invention, said cancer is selected from prostate cancer, breast cancer, lung cancer, uterus cancer, pancreatic cancer, liver cancer, renal cancer, ovarian cancer, colon cancer, stomach cancer, skin cancer, cerebral tumor, malignant myeloma and lymphoproliferative tumors. In one embodiment of the invention, said disease mediated through TLR7 is asthma, COPD, allergic rhinitis, allergic conjunctivitis, atopic dermatitis, hepatitis B, hepatitis C, HIV, HPV, bacterial infections or dermatosis.

According to a further aspect of the invention, there is provided the use of a compound of Formula (I) as defined hereinbefore, or a pharmaceutically acceptable salt thereof for the preparation of a medicament for the treatment of a disease mediated through TLR7. In one embodiment of the invention, said disease mediated through TLR7 is cancer. In a further embodiment of the invention, said cancer is selected from prostate cancer, breast cancer, lung cancer, uterus cancer, pancreatic cancer, liver cancer, renal cancer, ovarian cancer, colon cancer, stomach cancer, skin cancer, cerebral tumor, malignant myeloma and lymphoproliferative tumors. In one embodiment of the invention, said disease mediated through TLR7 is asthma, COPD, allergic rhinitis, allergic conjunctivitis, atopic dermatitis, hepatitis B, hepatitis C, HIV, HPV, bacterial infections or dermatosis.

According to a further aspect of the invention, there is provided the use of a compound of Formula (I) as defined hereinbefore, or a pharmaceutically acceptable salt thereof, for the preparation of a medicament for the treatment of cancer. In one embodiment of the invention, said cancer is selected from prostate cancer, breast cancer, lung cancer, uterus cancer, pancreatic cancer, liver cancer, renal cancer, ovarian cancer, colon cancer, stomach cancer, skin cancer, cerebral tumor, malignant myeloma and lymphoproliferative tumors.

According to a further aspect of the invention, there is provided the use of a compound of Formula (I) as defined hereinbefore, or a pharmaceutically acceptable salt thereof, for the preparation of a medicament for the treatment of asthma, COPD, allergic rhinitis, allergic conjunctivitis, atopic dermatitis, hepatitis B, hepatitis C, HIV, HPV, bacterial infections or dermatosis.

In one aspect of the invention there is provided the a compound of Formula (I) or a pharmaceutically acceptable salt thereof for use in the treatment of cancer.

According to a further aspect of the invention, there is provided a method of using a compound of Formula (I) as defined hereinbefore, or a pharmaceutically acceptable salt thereof, for the treatment of cancer. In one embodiment of the invention, said cancer is selected from prostate cancer, breast cancer, lung cancer, uterus cancer, pancreatic cancer, liver cancer, renal cancer, ovarian cancer, colon cancer, stomach cancer, skin cancer, cerebral tumor, malignant myeloma and lymphoproliferative tumors.

According to a further aspect of the invention, there is provided a method of using a compound of Formula (I) as defined hereinbefore, or a pharmaceutically acceptable salt thereof, for the treatment of asthma, COPD, allergic rhinitis, allergic conjunctivitis, atopic dermatitis, hepatitis B, hepatitis C, HIV, HPV, bacterial infections or dermatosis.

According to a further aspect of the invention, there is provided a method of treating a human suffering from a disease in which activation of TLR7 is beneficial, comprising the steps of administering to a person in need thereof of a therapeutically effective amount of a compound of Formula (I) as defined hereinbefore, or a pharmaceutically acceptable salt thereof. In one embodiment of the invention, the disease in which activation of TLR7 is beneficial is cancer. In a further embodiment of the invention, said cancer is selected from prostate cancer, breast cancer, lung cancer, uterus cancer, pancreatic cancer, liver cancer, renal cancer, ovarian cancer, colon cancer, stomach cancer, skin cancer, cerebral tumor, malignant myeloma and lymphoproliferative tumors. In one embodiment of the invention, the disease in which activation of TLR7 is beneficial is asthma, COPD, allergic rhinitis, allergic conjunctivitis, atopic dermatitis, hepatitis B, hepatitis C, HIV, HPV, bacterial infections or dermatosis.

In any aspect or embodiment described herein the cancer may be prostate cancer.

In any aspect or embodiment described herein the cancer may be breast cancer.

In any aspect or embodiment described herein the cancer may be lung cancer.

In any aspect or embodiment described herein the cancer may be uterus cancer.

In any aspect or embodiment described herein the cancer may be pancreatic cancer.

In any aspect or embodiment described herein the cancer may be liver cancer.

In any aspect or embodiment described herein the cancer may be renal cancer.

In any aspect or embodiment described herein the cancer may be ovarian cancer.

In any aspect or embodiment described herein the cancer may be colon cancer.

In any aspect or embodiment described herein the cancer may be stomach cancer.

In any aspect or embodiment described herein the cancer may be skin cancer.

In any aspect or embodiment described herein the cancer may be cerebral tumor.

In any aspect or embodiment described herein the cancer may be malignant myeloma cancer.

In any aspect or embodiment described herein the cancer may be lymphoproliferative tumors.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5 a-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (crlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, approaches to decrease the function of immune suppressive cells such as regulatory T cells, myeloid-derived suppressor cells or IDO (indoleamine 2,3,-deoxygenase)-expressing dendritic cells, and approaches using cancer vaccines consisting of proteins or peptides derived from tumour-associated antigens such as NY-ESO-1, MAGE-3, WT1 or Her2/neu.

According to this aspect of the invention there is provided a pharmaceutical product comprising a compound of the formula (I) as defined hereinbefore and an additional anti-tumour substance as defined hereinbefore for the conjoint treatment of cancer.

According to this aspect of the invention there is provided a combination suitable for use in the treatment of cancer comprising a compound of Formula (I) as defined hereinbefore, or a pharmaceutically acceptable salt thereof, and any one of the anti tumour agents listed under (i)-(ix) above.

Therefore in a further aspect of the invention there is provided a compound of Formula (I), or a pharmaceutically acceptable salt thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of Formula (I), or a pharmaceutically acceptable salt thereof, in combination with an anti-tumour agent selected from one listed under (i)-(ix) herein above, in association with a pharmaceutically acceptable diluent or carrier.

According to a further aspect of the invention there is provided a pharmaceutical composition which comprises a compound of Formula (I), or a pharmaceutically acceptable salt thereof, in combination with an anti-tumour agent selected from one listed under (i)-(ix) herein above, in association with a pharmaceutically acceptable diluent or carrier for use in the treatment of cancer.

According to another feature of the invention there is provided the use of a compound of the Formula (I), or a pharmaceutically acceptable salt thereof, in combination with an anti-tumour agent selected from one listed under (i)-(ix) herein above, in the manufacture of a medicament for use in cancer in a warm-blooded animal, such as man.

According to another feature of the invention there is provided a compound of the Formula (I), or a pharmaceutically acceptable salt thereof, in combination with an anti-tumour agent selected from one listed under (i)-(ix) herein above for use in the treatment of cancer in a warm-blooded animal, such as man.

Therefore in an additional feature of the invention, there is provided a method of treating cancer in a warm-blooded animal, such as man, in need of such treatment which comprises administering to said animal an effective amount of a compound of Formula (I), or a pharmaceutically acceptable salt thereof, in combination with an anti-tumour agent selected from one listed under (i)-(ix) herein above.

According to a further aspect of the present invention there is provided a kit comprising a compound of Formula (I), or a pharmaceutically acceptable salt thereof, in combination with an anti-tumour agent selected from one listed under (i)-(ix) herein above.

According to a further aspect of the present invention there is provided a kit comprising:
a) a compound of Formula (I), or a pharmaceutically acceptable salt thereof, in a first unit dosage form;
b) an anti-tumour agent selected from one listed under (i)-(ix) herein above; in a second unit dosage form; and
c) container means for containing said first and second dosage forms.

In one aspect of the invention the compounds of Formula (I) may be useful as vaccine adjuvants.

As a further aspect of the invention there is provided a compound of formula (I), or a pharmaceutically acceptable salt thereof, as defined herein, for use as a vaccine adjuvant.

As a further aspect of the invention there is provided the use of a compound of formula (I), or a pharmaceutically acceptable salt thereof, as defined herein, as a vaccine adjuvant, in the manufacture of a vaccine for the treatment of a disease or condition.

The invention still further provides a method of treating, or reducing the risk of, a disease or condition, which method comprises administering to a patient in need thereof a therapeutically effective amount of a vaccine and a compound of formula (I), or a pharmaceutically acceptable salt thereof, as defined herein.

The invention still further provides a method of increasing the response to a vaccine in a patient, which method comprises administering to a patient in need thereof a therapeutically effective amount of a vaccine and a compound of formula (I), or a pharmaceutically acceptable salt thereof, as defined herein.

EXAMPLES

The invention will now be illustrated with the following Examples in which generally, unless stated otherwise, all starting materials are commercially available. All solvents and commercial reagents used in the Examples were of laboratory grade and were used as received. All operations were carried out at ambient temperature, i.e. in the range 17 to 28° C., typically 20° C., and where appropriate, under an atmosphere of an inert gas such as nitrogen. 'Microwave' heating refers to heating to constant temperature, using variable power microwave irradiation in a CEM Discover™ microwave reactor. Hydrogenation reactions were carried out using a Büchi Peteric™ system or a ThalesNano H-Cube™ system, as detailed. Concentration of all solutions was carried out by evaporation under reduced pressure (in vacuo), e.g. using a Büchi Rotavapor™ rotary evaporator.

Thin Layer Chromatography (TLC) was carried out using aluminium- or glass-backed plates coated with silica (particle size <63 µm; porosity 60 Å; surface area ~500 m$^2$/g), with a fluorescent (UV$_{254}$) indicator. Following elution, the plates were visualized by either UV$_{254}$ irradiation, or developed with a suitable indicator, such as iodine (pre-absorbed onto silica), an aqueous solution of potassium permanganate, or an aqueous solution of cerium (IV) ammonium nitrate. Examples of indicator preparations can be found in 'Experimental Organic Chemistry: Preparative and Microscale' 2$^{nd}$ Ed. (Harwood, L., Moody, C. and Percy, J.), WileyBlackwell, 1998.

Analytical HPLC was carried out using either a Waters XBridge™ C8 3.5 µm column eluting with a gradient of MeCN in either 0.1% aqueous trifluoroacetic acid, 0.1% aqueous formic acid, 0.1% aqueous ammonium acetate or 0.1% aqueous NH$_3$; a Waters XBridge™ C18 3.5 µm column with a gradient of MeCN in 0.1% aqueous NH$_3$; a Waters Symmetry™ C18 3.5 µm column with a gradient of MeCN in 0.1% aqueous trifluoroacetic acid; a Waters Sunfire™ C8 3.5 µm column with a gradient of MeCN in 0.1% aqueous trifluoroacetic acid; or a Phenomenex Gemini™ C18 3 µm column with a gradient of MeCN in 0.1% aqueous trifluoroacetic acid. UV spectra of the eluted peaks were measured using a diode array on an Agilent 1100™ system, or equivalent.

Medium pressure liquid chromatography (MPLC) on silica (particle size <63 µm; porosity 60 Å; surface area ~500 m$^2$/g) was carried out using pre-packed Biotage FLASH™ columns or equivalent, e.g. Thomson SINGLE StEP™, Biotage Isolute™, Teledyne Isco RediSep™, or Silicycle UltraPure silica columns at recommended solvent flow rates and sample loadings. Fraction purity was determined by either TLC or analytical HPLC.

Preparative HPLC was carried out using either a Phenomenex Gemini™ C18 5 µm column, a Waters Sunfire™ C18 5 µm column, a Waters XBridge™ C8 5 µm column or a Waters XTerra™ 5 µm, unless otherwise detailed, using either MeCN in aqueous 0.1-0.2% trifluoroacetic acid, MeCN in aqueous 0.1-0.2% ammonium acetate, or MeCN in an aqueous 0.1-0.2% NH$_3$ solution as eluent, as detailed. Fractions were collected following detection by UV spectroscopy at a wavelength such as 220 or 254 nm. Fraction purity was determined by either TLC or analytical HPLC.

Proton nuclear magnetic resonance ($^1$H NMR) spectra were recorded on Bruker Avance 600 (600 MHz), a Bruker DRX 500 (500 MHz) or a Varian UnityInova 500 MHz, 400 MHz or 300 MHz instrument. Either the central peaks of chloroform-d (CDCl$_3$; $\delta_H$ 7.27 ppm), dimethylsulfoxide-d$_6$ (d$_6$-DMSO; $\delta_H$ 2.50 ppm) or an internal standard of tetramethylsilane (TMS; $\delta_H$ 0.00 ppm) were used as references. Unless otherwise specified, $^1$H NMR spectra were determined using deuterated DMSO. The following abbreviations are used for NMR data: s=singlet, d=doublet, t=triplet, q=quartet, m=multiplet, dd=doublet of doublets, tt=triplet of triplets, br=broad, quintet=qn. Mass spectra were recorded on an Agilent MSD or similar equipment (+ve and -ve APCI and/or electrospray (unless otherwise stated: in "multimode +")) following analytical HPLC.

All other processes were carried out using standard laboratory techniques, e.g. as detailed in 'Experimental Organic Chemistry: Preparative and Microscale' 2$^{nd}$ Ed. (Harwood, L., Moody, C. and Percy, J.), WileyBlackwell, 1998.

The following abbreviations may be used in the scientific parts of this specification: EtOAc=ethyl acetate; DCM=dichloromethane; NMP=N-methylpyrrolidinone; DMF=N,N-dimethylformamide; DMSO=dimethylsulfoxide; THF=tetrahydrofuran; MeOH=methanol; EtOH=ethanol; MeCN=acetonitrile; Pd/C=palladium on carbon; DMAP=4-dimethylaminopyridine; sat.=saturated; aq.=aqueous; DMA=N,N-dimethyl-acetamide; conc.=concentrated; r.t.=room temperature; h=hours; min(s)=mins.; M=molar; MS=mass spectrometry; APCI=atmospheric chemical ionisation method; ESI=electron spray ionisation method; SCX=Solid phase extraction with a sulfonic acid sorbent; HPLC=High performance liquid chromatography; RPHPLC=Reverse-phase high performance liquid chromatography; FCC=flash column chromatography using silica; DIPEA=diisopropylethylamine.

Example 1

5-(4-Methoxybenzyl)-6-methyl-N$^4$-pentylpyrimidine-2,4-diamine (i) 2-(4-Methoxy-benzyl)-3-oxo-butyric acid ethyl ester Ethyl acetoacetate (11.7 mL) was added to a solution of 4-methoxy-benzaldehyde (10.0 g) in toluene (150 mL). Piperidine (0.80 mL) and acetic acid (2.30 mL) were then added and the mixture was heated at reflux for 20 h. The solvent was then removed and the resulting orange oil was dissolved in EtOH (0.30 L) and 10% Pd/C (0.50 g) was added and stirred under H$_2$ (2 bar) for 3 h. The reaction mixture was filtered through diatomaceous earth (Celite™) and the solvent removed by evaporation. The crude product was purified by FCC to give the subtitle compound as an oil (12.7 g); $^1$H NMR: 7.19 (1H, t), 6.75 (3H, m), 4.15 (2H, q), 3.78 (4H, m), 3.13 (2H, d), 2.20 (3H, s), 1.26 (3H, t); LC-MS m/z 249 ESI.

(ii) 2-Amino-5-(4-methoxy-benzyl)-6-methyl-pyrimidin-4-ol

Guanidium carbonate (3.90 g) was added to a solution of the product from step (I) (5.30 g) in ethanol (50.0 mL) and heated at 80° C. for 15 h. After cooling the product was filtered off as a solid, this was suspended in water and collected by filtration, washed with EtOAc and dried to give the subtitle compound (3.40 g); $^1$H NMR: 10.83 (1H, s), 7.08 (2H, d), 6.79 (2H, d), 6.34 (2H, s), 3.69 (3H, s), 3.56 (2H, s), 2.00 (3H, s); LC-MS m/z 246 ESI.

(iii) 4-Chloro-5-(4-methoxy-benzyl)-6-methyl-pyrimidin-2-ylamine

The product of step (ii) (1.00 g) was added to POCl$_3$ (10.0 mL) and the mixture was heated at 100° C. for 15 h. The solvent was removed and the residue diluted with water and adjusted to pH 7 with sat NaHCO$_3$. This mixture was heated at 50° C. for 2 h, then extracted with EtOAc, dried and solvent removed to give the subtitle compound as a white solid (0.71 g); $^1$H NMR: 7.02 (2H, d), 6.85 (2H, d), 6.84 (2H, s), 3.88 (2H, s), 3.71 (3H, s), 2.21 (3H, s); LC-MS m/z 263 ESI.

(iv) 5-(4-Methoxy-benzyl)-6-methyl-N$^4$-pentyl-pyrimidine-2,4-diamine

To the product of step (iii) (3.00 g) in dioxane (30.0 mL), pentylamine (5.30 mL) was added and the mixture was heated at 100° C. for 48 h. The solvent was removed and the residue was dissolved in EtOAc and washed with sat. NaHCO$_3$, dried and solvent removed. The crude compound was purified by FCC to give the title compound as a white solid (2.30 g); $^1$H NMR: 7.02 (2H, d), 6.81 (2H, d), 6.31-6.22 (1H, m), 5.83 (2H, s), 3.69 (3H, s), 3.66 (2H, s), 3.25 (2H, q), 2.03 (3H, s), 1.43 (2H, q), 1.28-1.06 (4H, m), 0.81 (3H, t); LC-MS m/z 315.

Example 2

4-(2-Amino-4-methyl-6-pentylamino-pyrimidin-5-ylmethyl)-phenol

A solution of BBr$_3$ (1M in DCM, 14.6 mL) was added to a solution of the product of Example 1 (2.30 g) in DCM at 0° C. and stirred for 1 h. Ice and water were added and the mixture was stirred for 30 min, then the organic phase was separated, the aqueous layer was extracted with EtOAc, and the combined organics were dried and the solvent was removed by evaporation. The crude product was purified by FCC to give the title compound as a cream solid (1.11 g); $^1$H NMR: 11.96 (1H, s), 7.57 (1H, s), 7.07 (2H, s), 6.93 (2H, d), 6.67 (2H, d), 3.69 (2H, s), 3.38-3.32 (2H, m), 2.16 (3H, s), 1.46 (2H, q), 1.27-1.18 (2H, m), 1.15-1.07 (2H, m), 0.82 (3H, t); LC-MS m/z 301.

Example 3

5-(4-(2-(Dimethylamino)ethoxy)benzyl)-6-methyl-N-pentylpyrimidine-2,4-diamine

To a suspension of the product of Example 2 (0.10 g) in DMF (2.00 mL), Cs$_2$CO$_3$ (0.24 g) was added and stirred at r.t. for 30 min. A mixture of 2-dimethylaminoethylchloride hydrochloride (0.096 g), Cs$_2$CO$_3$ (0.24 g) and NaI (0.05 g) was also stirred for 30 min and the two mixtures combined and heated at 110° C. for 2 h. The reaction was filtered, diluted with water, extracted with EtOAc, dried and the solvent removed. The crude product was purified by RPHPLC to afford the title compound as a colourless oil (0.035 g); $^1$H NMR: 7.00 (2H, d), 6.81 (2H, d), 6.04 (1H, t), 5.62 (2H, s), 3.97 (2H, t), 3.65 (2H, s), 3.24 (2H, q), 2.57 (2H, t), 2.19 (6H, s), 2.01 (3H, s), 1.43 (2H, qn), 1.27-1.08 (4H, m), 0.81 (3H, t); LC-MS m/z 372.

Example 4

5-(4-(3-(Dimethylamino)propoxy)benzyl)-6-methyl-N-pentylpyrimidine-2,4-diamine

The title compound was prepared by the method of Example 3 using dimethylamino-propylchloride hydrochloride (0.105 g) to give the product as a colourless oil (0.039 g); $^1$H NMR: 7.02 (2H, d), 6.81 (2H, d), 6.53 (1H, s), 6.10 (2H, s), 3.93 (2H, t), 3.68 (2H, s), 3.30-3.24 (2H, m), 2.53-2.48 (2H, m), 2.27 (6H, s), 2.06 (3H, s), 1.86 (2H, qn), 1.43 (2H, qn), 1.26-1.06 (4H, m), 0.81 (3H, t); LC-MS m/z 386.

Example 5

6-Methyl-$N^4$-pentyl-5-(4-(2-(piperidin-1-yl)ethoxy)benzyl)pyrimidine-2,4-diamine The title compound was prepared by the method of Example 3 using N-(2-chloroethyl)-piperidine hydrochloride (0.12 g) to give the product as a white solid (0.058 g); $^1$H NMR: 7.00 (2H, d), 6.81 (2H, d), 6.03 (1H, t), 5.61 (2H, s), 3.98 (2H, t), 3.65 (2H, s), 3.23 (2H, q), 2.60 (2H, t), 2.42-2.37 (4H, m), 2.01 (3H, s), 1.50-1.33 (8H, m), 1.26-1.18 (2H, m), 1.16-1.07 (2H, m), 0.81 (3H, t); LC-MS m/z 412.

Example 6

6-Methyl-$N^4$-pentyl-5-(4-(2-(pyrrolidin-1-yl)ethoxy)benzyl)pyrimidine-2,4-diamine The title compound was prepared by the method of Example 3 using N-(2-chloroethyl)-pyrrolidine hydrochloride (0.115 g) to give the product as a colourless oil (0.035 g). $^1$H NMR: 7.00 (2H, d), 6.81 (2H, d), 6.04 (1H, t), 5.61 (2H, s), 3.99 (2H, t), 3.65 (2H, s), 3.24 (2H, q), 2.74 (2H, t), 2.37-2.20 (4H, m), 2.02 (3H, s), 1.69-1.63 (4H, m), 1.48-1.37 (2H, m), 1.27-1.08 (4H, m), 0.81 (3H, t); LC-MS m/z 398.

Example 7

5-(4-(2-(Benzyl(methyl)amino)ethoxy)benzyl)-6-methyl-$N^4$-pentyl-pyrimidine-2,4-diamine The title compound was prepared by the method of Example 3 using N-(2-chloroethyl)-N-methylbenzylamine hydrochloride (0.147 g) to give the product as a colourless oil (0.032 g); $^1$H NMR: 7.35-7.18 (5H, m), 7.00 (2H, d), 6.81 (2H, d), 6.05 (1H, t), 5.62 (2H, s), 4.10-4.01 (2H, m), 3.65 (2H, s), 3.55 (2H, s), 3.24 (2H, q), 2.70 (2H, t), 2.21 (3H, s), 2.01 (3H, s), 1.43 (2H, qn), 1.27-1.09 (4H, m), 0.81 (3H, t); LC-MS m/z 448.

Example 8

3-(4-((2-Amino-4-methyl-6-(pentylamino)pyrimidin-5-yl)methyl)-phenoxy)propan-1-ol To a suspension of the product of Example 2 (0.35 g) in DMF (10.0 mL), $Cs_2CO_3$ (0.25 g) was added and the mixture was stirred at r.t. for 30 min. 3-Bromo-1-propanol (0.158 mL) and NaI (0.05 g) were added and the mixture was heated at 100° C. for 9 h. The reaction was diluted with water, extracted with EtOAc, dried and the solvent removed. The crude product was purified by FCC eluting with 10:1 DCM-MeOH to afford the title compound as a colourless oil (0.24 g) which solidified upon standing; $^1$H NMR: 7.00 (2H, d), 6.80 (2H, d), 6.05 (1H, t), 5.62 (2H, s), 4.50 (1H, t), 3.96 (2H, t), 3.64 (2H, s), 3.53 (2H, q), 3.24 (2H, q), 2.01 (3H, s), 1.82 (2H, qn), 1.43 (2H, qn), 1.28-1.17 (2H, m), 1.17-1.07 (2H, m), 0.82 (3H, t); LC-MS m/z 359.

Example 9

6-Methyl-$N^4$-pentyl-5-(4-(3-(pyrrolidin-1-yl)propoxy)benzyl)pyrimidine-2,4-diamine (i) 5-(4-(3-Chloropropoxy)benzyl)-6-methyl-$N^4$-pentylpyrimidine-2,4-diamine To a solution the product of Example 8 (0.32 g) in DCM (5 mL), $SOCl_2$ (0.5 mL) was added and the solution was stirred at r.t. for 36 h. The solvent was removed and the crude material was purified by FCC eluting with DCM and then 20:1 DCM-MeOH to give the subtitle compound as an orange oil (0.124 g); $^1$H NMR: 7.88 (1H, t), 7.07 (2H, d), 6.87 (2H, d), 4.04 (2H, t), 3.79-3.74 (4H, m), 3.36-3.25 (2H, m), 2.20 (3H, s), 2.17-2.10 (2H, m), 1.51-1.43 (2H, m), 1.27-1.15 (2H, m), 1.12-1.02 (2H, m), 0.80 (3H, t).

(ii) 6-Methyl-$N^4$-pentyl-5-(4-(3-(pyrrolidin-1-yl)propoxy)benzyl)pyrimidine-2,4-diamine To a suspension of triethylamine (0.09 mL), NaI (0.01 g) and the product of step (i) (0.04 g) in DMF (2 mL) was added pyrrolidine (0.027 mL). The mixture was heated at 80° C. for 15 h, then cooled to r.t., diluted with water, extracted with EtOAc, dried and the solvent removed. The crude product was purified by RPHPLC to afford the title compound as an orange oil (7 mg); $^1$H NMR: 7.86 (s, 1H), 7.41 (s, 2H), 7.07 (d, 2H), 6.86 (d, 2H), 4.00 (t, 2H), 3.76 (s, 2H), 3.22 (t, 2H), 3.17 (s, 2H), 2.19 (s, 3H), 2.15-2.06 (m, 2H), 2.02-1.83 (m, 4H), 1.30-1.15 (m, 4H), 1.15-1.03 (m, 6H), 0.81 (t, 3H); LC-MS m/z 412.

Example 10

6-Methyl-5-(4-(3-(4-methylpiperazin-1-yl)propoxy)benzyl)-V-pentylpyrimidine-2,4-diamine The title compound was prepared by the method of Example 9 step (ii) using the product of Example 9 step (i) (0.04 g) and 1-methylpiperazine (0.0354 mL) to give the product as a yellow oil (9 mg); $^1$H NMR 7.00 (2H, d), 6.79 (2H, d), 6.02 (1H, t), 5.61 (2H, s), 3.92 (2H, t), 3.64 (2H, s), 3.23 (2H, q), 2.42-2.24 (10H, m), 2.13 (3H, s), 2.01 (3H, s), 1.81 (2H, qn), 1.42 (2H, qn), 1.28-1.16 (2H, m), 1.16-1.06 (2H, m), 0.81 (3H, t); LC-MS m/z 441.

Example 11

5-(4-(3-(Dimethylamino)propoxy)-2-methoxybenzyl)-6-methyl-$N^4$-pentylpyrimidine-2,4-diamine (i) 4-(3-(Dimethylamino)propoxy)-2-methoxybenzaldehyde 3-Dimethylaminopropylchloride hydrochloride (2.493 g) and NaI (0.394 g) were added to 4-hydroxy-2-methoxybenzaldehyde (2 g) and $Cs_2CO_3$ (12.85 g) in DMF (50 mL). The resulting suspension was stirred at 100° C. for 1 h. The reaction mixture was filtered and diluted with EtOAc (100 mL). The organic phase was washed with water and brine, dried, filtered and concentrated by evaporation to afford the subtitle compound as a yellow oil (2.23 g); $^1$H NMR: 10.17 (1H, s), 7.65 (1H, d), 6.67 (1H, d), 6.64 (1H, dd), 4.12 (2H, t), 3.90 (3H, s), 2.35 (2H, t), 2.14 (6H, s), 1.87 (2H, qn).

(ii) Ethyl 2-(4-(3-(dimethylamino)propoxy)-2-methoxybenzylidene)-3-oxobutanoate

Ethyl acetoacetate (1.489 mL), piperidine (0.047 mL) and acetic acid (0.145 mL) were added to a solution of the product from step (i) (2.23 g) in toluene (50 mL), and the mixture was stirred at 110° C. for 5 days. The solvent was removed under reduced pressure to afford the subtitle compound (3.57 g) that was used in the next step without purification.

(iii) Ethyl 2-(4-(3-(dimethylamino)propoxy)-2-methoxybenzyl)-3-oxobutanoate

A suspension of the product from step (ii) (3.57 g) and 10% Pd/C (0.2 g) in EtOH (50 mL) was hydrogenated under 3 bar at r.t. for 16 h. The reaction mixture was filtered through diatomaceous earth (Celite™) and the filtrate was concentrated by evaporation. The crude product was purified by FCC eluting with 0-10% MeOH in EtOAc to afford the subtitle compound (1.25 g) as a yellow oil; $^1$H NMR: 6.95 (1H, d), 6.51 (1H, d), 6.40 (1H, dd), 4.10-4.00 (2H, m), 3.96 (2H, t), 3.83 (1H, t), 3.77 (3H, s), 3.01-2.81 (2H, m), 2.34 (2H, t), 2.14 (9H, s), 1.82 (2H, qn), 1.12 (3H, t).

(iv) 2-Amino-5-(4-(3-(dimethylamino)propoxy)-2-methoxybenzyl)-6-methylpyrimidin-4-ol Guanidine carbonate (0.716 g) was added in one portion to a solution of the product from step (iii) (1.25 g) in EtOH (20 mL) and the mixture was stirred at 80° C. for 15 h. The solvent was evaporated, the residue diluted with EtOAc (20 mL), washed with water, dried and evaporated. The residue was suspended in hexane-EtOAc (5:1; 20 mL) and the solid was collected by filtration to afford the subtitle compound as a pale yellow solid (0.87 g); $^1$H NMR: 6.72 (d, 1H), 6.60 (s, 2H), 6.48 (d, 1H), 6.35 (dd, 1H), 3.93 (t, 2H), 3.78 (s, 3H), 3.46 (s, 2H), 2.33 (t, 2H), 2.13 (s, 6H), 1.90 (s, 3H), 1.84-1.78 (m, 2H).

(v) 4-Chloro-5-(4-(3-(dimethylamino)propoxy)-2-methoxybenzyl)-6-methylpyrimidin-2-amine The subtitle compound was prepared using the method of Example 1 step (iii) and the product of step (iv) to give a tan solid (0.71 g); $^1$H NMR: 6.83 (s, 2H), 6.57 (d, 1H), 6.54 (d, 1H), 6.41 (dd, 1H), 4.00 (t, 2H), 3.81 (s, 3H), 3.75 (s, 2H), 3.05-2.95 (m, 2H), 2.63 (s, 6H), 2.15 (s, 3H), 2.11-2.01 (m, 2H).

(vi) 5-(4-(3-(Dimethylamino)propoxy)-2-methoxybenzyl)-6-methyl-$N^4$-pentylpyrimidine-2,4-diamine Amylamine (0.127 mL) was added to a solution of the product from step (v) (100 mg) in NMP (2 mL) and stirred at 150° C. for 15 h. The mixture was diluted with EtOAc (10 mL) washed with sat. NaHCO$_3$ (10 mL), water (10 mL), and sat. brine (10 mL) dried, and the solvent removed by evaporation. The crude product was purified by RPHPLC and then trituration with diethyl ether gave the title compound as a white solid (8 mg); $^1$H NMR: 6.60 (d, 1H), 6.53 (d, 1H), 6.37 (dd, 1H), 5.86 (t, 1H), 5.61 (s, 2H), 3.93 (t, 2H), 3.82 (s, 3H), 3.52 (s, 2H), 3.21 (q, 2H), 2.35-2.30 (m, 2H), 2.12 (s, 6H), 1.98 (s, 3H), 1.80 (q, 2H), 1.46-1.36 (m, 2H), 1.28-1.18 (m, 2H), 1.17-1.08 (m, 2H), 0.82 (t, 3H); LC-MS m/z 416.

The title compound can also be made by the following method:

Methanesulfonyl chloride (0.040 mL) was added to the mixture of the product from Example 36 (0.17 g) and triethylamine (0.072 mL) in THF (5 mL) at 0° C. and the mixture was stirred for 30 min. Sat. NaHCO$_3$ was added and the mixture was extracted twice with CHCl$_3$, then the combined organic layers were dried and concentrated. The residue was dissolved in DMF (5 mL), then dimethylamine (40% aq. solution, 2 mL) was added and the mixture was stirred at r.t. for 18 h. The mixture was then treated with 4% NH$_3$ solution and brine and extracted twice with EtOAc. The combined organic layers were washed twice with brine, dried and concentrated. The residue was purified by FCC to give the title compound as a white solid (0.10 g); $^1$H NMR: 6.61 (d, 1H), 6.53 (d, 1H), 6.37 (dd, 1H), 6.18 (br t, 1H), 5.91 (brs, 2H), 3.94 (t, 2H), 3.82 (s, 3H), 3.53 (s, 2H), 3.22 (q, 2H), 2.42 (t, 2H), 2.20 (s, 6H), 2.00 (s, 3H), 1.85 (tt, 2H), 1.42 (tt, 2H), 1.24 (m, 2H), 1.13 (m, 2H), 0.82 (t, 3H); LC-MS m/z 415 ESI.

Example 12

Methyl 4-((2-amino-4-methyl-6-(pentylamino)pyrimidin-5-yl)methyl)-3-methoxybenzoate

(i) Methyl 4-(2-(ethoxycarbonyl)-3-oxobutyl)-3-methoxybenzoate

NaH (60% in mineral oil, 1.45 g) was added portionwise over 10 min to a solution of ethyl acetoacetate (4.4 mL) in THF (60 mL) at 0° C. and the mixture was stirred for 10 min. A solution of methyl 4-(bromomethyl)-3-methoxybenzoate (7.5 g) in THF (40 mL) was added and the mixture was warmed to 70° C. and stirred for 15 h. The reaction was poured into ice/water (300 mL) and stirred for 30 min. The aqueous mixture was extracted with EtOAc, dried and concentrated by evaporation to afford the subtitle compound. The reaction was repeated on an identical scale. The two batches of crude product were combined and purified by FCC eluting with 8:2 to 7:3 isohexane-EtOAc to afford the subtitle compound as a colourless oil (14.7 g); $^1$H NMR: 7.48 (dd, 1H), 7.45 (d, 1H), 7.24 (d, 1H), 4.05 (q, 2H), 3.95 (dd, 1H), 3.86 (s, 3H), 3.84 (s, 3H), 3.10 (dd, 1H), 3.00 (dd, 1H), 2.17 (s, 3H), 1.09 (t, 3H).

(ii) Methyl 4-((2-amino-4-hydroxy-6-methylpyrimidin-5-yl)methyl)-3-methoxybenzoate The subtitle compound was formed using the method of Example 1 step (ii) and the product from step (i) (14.7 g) to give the subtitle compound as a colourless solid (8.6 g), which was used without further purification; $^1$H NMR: 10.78 (s, 1H), 7.46 (d, 1H), 7.45 (s, 1H), 6.98 (d, 1H), 6.34 (s, 2H), 3.89 (s, 3H), 3.83 (s, 3H), 3.61 (s, 2H), 1.93 (s, 3H); LC-MS m/z 304.

(iii) Methyl 4-((2-amino-4-chloro-6-methylpyrimidin-5-yl)methyl)-3-methoxybenzoate The subtitle compound was formed using the method of Example 1 step (iii) and the product from step (ii) (8.6 g) to give the subtitle compound as a colourless solid (9.05 g), which was used without further purification; $^1$H NMR: 7.50 (s, 2H), 7.49 (d, 1H), 6.90 (s, 1H), 6.81 (d, 1H), 3.92 (s, 3H), 3.90 (s, 3H), 3.84 (s, 2H), 2.16 (s, 3H).

(iv) Methyl 4-((2-amino-4-methyl-6-(pentylamino)pyrimidin-5-yl)methyl)-3-methoxybenzoate Pentylamine (7.22 mL) was added to a solution of the product of step (iii) (5 g) in NMP (80 mL) and the mixture was stirred at 150° C. for 15 h. The reaction mixture was cooled, diluted with EtOAc (200 mL), washed with water (3×200 mL), brine (100 mL), dried and concentrated by evaporation. The residue was suspended in diethyl ether (20 mL) and the solid produced was collected by filtration to give the title compound as a colourless solid (1.21 g); $^1$H NMR 7.48 (d, 1H), 7.45 (dd, 1H), 6.81 (d, 1H), 6.07 (t, 1H), 5.68 (s, 2H), 3.92 (s, 3H), 3.83 (s, 3H), 3.68 (s, 2H), 3.25-3.20 (m, 2H), 1.93 (s, 3H), 1.47-1.38 (m, 2H), 1.27-1.08 (m, 4H), 0.81 (t, 3H); LC-MS m/z 373.

Example 13

(S)-Methyl 4-((2-amino-4-(1-hydroxypentan-2-ylamino)-6-methyl-pyrimidin-5-yl)methyl)-3-methoxybenzoate (S)-Methyl 4-((2-amino-4-(1-hydroxypentan-2-ylamino)-6-methylpyrimidin-5-yl)methyl)-3-methoxybenzoate (S)-2-Aminopentan-1-ol (0.769 g) was added to a solution of the product from Example 12 step (iii) (1.2 g) in NMP (20 mL) and the mixture was stirred at 120° C. for 60 h. The reaction mixture was then cooled, diluted with EtOAc (50 mL), washed with saturated $NaHCO_3$ (2×50 mL), brine (50 mL), dried and concentrated by evaporation. The crude product was purified by FCC eluting with 20:1 to 10:1 DCM-MeOH to produce an orange oil (0.475 g). A 100 mg sample was further purified by RPHPLC to give the title compound as an orange gum (15 mg); $^1$H NMR: 7.48 (d, 1H), 7.46 (dd, 1H), 6.89 (d, 1H), 5.68 (s, 2H), 5.50 (d, 1H), 4.58-4.48 (m, 1H), 4.17-4.05 (m, 1H), 3.92 (s, 3H), 3.84 (s, 3H), 3.70 (s, 2H), 3.39-3.20 (m, 2H), 1.99 (s, 3H), 1.54-1.39 (m, 1H), 1.33-1.20 (m, 1H), 1.16-1.02 (m, 2H), 0.76 (t, 3H); LC-MS m/z 389.

Example 14

(S)-Methyl 4-((2-amino-4-(1-hydroxyheptan-3-ylamino)-6-methyl-pyrimidin-5-yl)methyl)-3-methoxybenzoate (i) (E)-tert-Butyl hept-2-enoate To a solution of valeraldehyde (5.81 g) in THF (100 mL) was added tert-butoxycarbonyl-methylenetriphenylphosphorane (25.4 g) and the mixture was stirred for 16 h at r.t. The solvents were removed by evaporation and the resulting residue was slurried in diethyl ether and then the mixture was filtered. The filtrate was concentrated by evaporation and the residue was purified by FCC eluting with 97:3 isohexane-EtOAc to give the subtitle compound (8.5 g); $^1$H NMR ($CDCl_3$): 6.86 (dt, 1H), 5.73 (dt, 1H), 2.25-2.09 (m, 2H), 1.47 (s, 9H), 1.47-1.27 (m, 4H), 0.90 (t, 3H).

(ii) (S)-tert-Butyl 3-(benzyl((S)-1-phenylethyl)amino)heptanoate n-Butyllithium (2.5 M in hexanes, 27.66 mL) was added to a stirred solution of (S)—N-benzyl-1-phenylethanamine (15.59 g) in THF (150 mL) at −78° C. The reaction mixture was stirred for 30 min then the product from step (i) (8.5 g) in THF (50 mL) was added and the reaction mixture was stirred for 2 h at −78° C. The mixture was quenched with sat. $NH_4Cl$ solution and warmed to r.t. The mixture was partitioned between EtOAc and water, the organic phase was washed with water, dried, and concentrated by evaporation. The residue was purified by FCC eluting with 95:5 isohexane-EtOAc to give the subtitle compound (12.7 g); $^1$H NMR ($CDCl_3$): 7.49-7.15 (m, 10H), 3.87-3.70 (m, 2H), 3.48 (d, 1H), 3.35-3.21 (m, 1H), 1.99-1.78 (m, 2H), 1.53 (s, 3H), 1.39 (s, 9H), 1.36-1.14 (m, 6H), 0.88 (t, 3H); LC-MS m/z 396 ESI.

(iii) (S)-3-(Benzyl((S)-1-phenylethyl)amino)heptanoic acid

The product from step (ii) (12 g) was dissolved in DCM (40 mL) and trifluoroacetic acid (2 mL) and the resulting mixture was stirred for 24 h. The solvents were removed by evaporation to give the subtitle compound (17 g); LC-MS m/z 340 ESI.

(iv) (S)-3-(Benzyl((S)-1-phenylethyl)amino)heptan-1-ol

The product from step (iii) (12 g) was dissolved in THF (120 mL) and borane-THF complex (1M in THF, 132.3 mL) was added dropwise. The mixture was then stirred at r.t. overnight then MeOH was added followed by 2 M HCl (20 mL). The mixture was concentrated by evaporation and the resulting residue was dissolved in MeOH and purified via SCX resin. The resulting residue was further purified via FCC eluting with 9:1 to 4:1 isohexane-EtOAc to give the subtitle compound (6 g); $^1$H NMR ($CDCl_3$): 7.45-7.13 (m, 10H), 4.00-3.91 (m, 1H), 3.85 (d, 1H), 3.69 (d, 1H), 3.56-3.43 (m, 1H), 3.27-3.15 (m, 1H), 2.84-2.71 (m, 1H), 2.61 (s, 1H), 1.77-1.63 (m, 1H), 1.55 (s, 2H), 1.47-1.20 (m, 8H), 0.93 (t, 3H); LC-MS m/z 326 ESI.

(v) (S)-3-Aminoheptan-1-ol

A solution of the product from step (iv) (5 g) and 5% Pd/C (0.5 g) in EtOH (25 mL) was hydrogenated using a pressure of 5 bar at r.t. for 5 days. A further portion of 5% Pd/C (1.50 g) was then added, and the mixture was hydrogenated using a pressure of 5 bar at r.t. for a further 1 day. The reaction mixture was then filtered and the solvent removed by evaporation to give the subtitle compound (1.8 g); $^1$H NMR ($CDCl_3$): 3.89-3.74 (m, 2H), 2.94-2.84 (m, 1H), 2.79-2.41 (m, 3H), 1.70-1.60 (m, 1H), 1.55-1.38 (m, 2H), 1.39-1.19 (m, 5H), 0.96-0.83 (m, 3H).

(vi) (S)-Methyl 4-((2-amino-4-(1-hydroxyheptan-3-ylamino)-6-methylpyrimidin-5-yl)methyl)-3-methoxybenzoate The title compound was prepared by the method of Example 13 using the product from Example 12 step (iii) (0.1 g) and the product of step (v) (0.08 g). The crude product was purified by RPHPLC to give the title compound as a colourless gum (9 mg); $^1$H NMR: 7.49 (d, 1H), 7.46 (dd, 1H), 6.90 (d, 1H), 6.44-6.25 (m, 2H), 4.39-4.33 (m, 1H), 4.29-4.20 (m, 1H), 3.93 (s, 3H), 3.84 (s, 3H), 3.74 (s, 2H), 3.30-3.28 (m, 2H), 2.03 (s, 3H), 1.66-1.47 (m, 2H), 1.47-1.32 (m, 2H), 1.29-0.97 (m, 4H), 0.76 (t, 3H); LC-MS m/z 417.

Example 15

(S)-4-(Dimethylamino)butyl 4-((2-amino-4-(1-hydroxypentan-2-yl-amino)-6-methylpyrimidin-5-yl)methyl)-3-methoxybenzoate benzenesulfonate salt (i) (S)-4-((2-Amino-4-(1-hydroxypentan-2-ylamino)-6-methylpyrimidin-5-yl)methyl)-3-methoxybenzoic acid (S)-2-Amino-1-pentanol (192 mg) was added to a stirred suspension of the product of Example 12 step (iii) (0.30 g) in butan-1-ol (2 mL) and the mixture was heated in a microwave at 180° C. for 2 h. 5M KOH (0.5 mL) was added and the mixture was then heated to 120° C. over a period of 1 h in a microwave. The mixture was then concentrated by evaporation and the residue was diluted with MeOH (2 mL). Glacial acetic acid was added dropwise until the pH~7 and the mixture was then purified by RPHPLC to give the subtitle compound as a colourless solid (53 mg); $^1$H NMR: 7.47 (d, 1H), 7.41 (dd, 1H), 6.85 (d, 1H), 5.74 (s, 2H), 5.52 (d, 1H), 4.15-4.06 (m, 1H), 3.90 (s, 3H), 3.68 (s, 2H), 3.38-3.33 (m, 1H), 3.28-3.22 (m, 1H), 2.02 (s, 3H), 1.52-1.41 (m, 1H), 1.32-1.21 (m, 3H), 1.15-1.03 (m, 2H), 0.76 (t, 3H); LC-MS m/z 375.

(ii) (S)-4-(Dimethylamino)butyl 4-((2-amino-4-(1-hydroxypentan-2-ylamino)-6-methylpyrimidin-5-yl)methyl)-3-methoxybenzoate benzene sulphonate A solution of 1-propanephosphonic acid cyclic anhydride (0.35 mL) (1.57 M in THF) was added to a suspension of the product of step (i) (69 mg), triethylamine (0.077 mL), 4-(dimethylamino)-1-butanol (0.12 mL) and 4-dimethylaminopyridine (4.50 mg) in DMF (2 mL). The mixture was stirred at r.t. for 60 h and was then diluted with EtOAc (10 mL). The solution was washed with water (2×10 mL) dried and concentrated by evaporation. The crude product was purified by RPHPLC to produce a colourless gum which was dissolved in McCN (0.5 mL). Benzenesulphonic acid (7.9 mg) was added and the solvent was evaporated to give a residue which was triturated with diethyl ether to give the title compound as a colourless solid (27.0 mg); $^1$H NMR: 7.61-7.58 (m, 1H), 7.48-7.45 (m, 3H), 7.34-7.27 (m, 5H), 6.93 (d, 1H), 6.21-6.06 (m, 1H), 4.63-4.57 (m, 1H), 4.27 (t, 2H), 4.20-4.12 (m, 1H), 3.92 (s, 3H), 3.73 (s, 2H), 3.41-3.33 (m, 4H), 2.42 (s, 6H), 2.03 (s, 3H), 1.77-1.67 (m, 2H), 1.66-1.57 (m, 1H), 1.53-1.43 (m, 1H), 1.34-1.21 (m, 2H), 1.15-1.03 (m, 2H), 0.77 (t, 3H); LC-MS m/z 474.

Example 16

Methyl 3-((2-amino-4-methyl-6-(pentylamino)pyrimidin-5-yl)methyl)-4-methoxybenzoate

(i) Methyl 3-(bromomethyl)-4-methoxybenzoate

Methyl 4-methoxy-3-methylbenzoate (16 g) was dissolved in EtOAc (100 mL) and then N-bromosuccinimide (18.96 g) and 2,2'-azobisisobutyronitrile (1 g) were added. The mixture was then heated to 80° C. for 4 h. After cooling to r.t. sat. sodium thiosulfate solution was added, the organic phase was separated, washed with brine, dried and the solvents removed by evaporation. The crude product was dissolved in mixture of isohexane-EtOAc (9:1) and a solid was produced which was collected to give the subtitle compound (11.82 g); $^1$H NMR (CDCl$_3$): 8.05-7.98 (m, 2H), 6.91 (d, 1H), 4.55 (s, 2H), 3.96 (s, 3H), 3.89 (s, 3H). LC-MS m/z 260.

(ii) Methyl 3-((2-amino-4-methyl-6-(pentylamino)pyrimidin-5-yl)methyl)-4-methoxybenzoate The title compound was prepared using the product from step (i) (11.82 g) and the method of Example 12 steps (i)-(iv) to give a solid product (2.0 g); $^1$H NMR: 7.83 (d, 1H), 7.32 (s, 1H), 7.11 (d, 1H), 6.08 (s, 1H), 5.69 (s, 2H), 3.94 (s, 3H), 3.73 (s, 3H), 3.63 (s, 2H), 3.25-3.07 (m, 2H), 1.93 (s, 3H), 1.50-1.33 (m, 2H), 1.25-1.01 (m, 4H), 0.79 (t, 3H); LC-MS m/z 373.

Example 17

Methyl 3-((2-amino-4-methyl-6-(pentylamino)pyrimidin-5-yl)methyl)-4-fluorobenzoate

(i) Methyl 4-fluoro-3-methylbenzoate

SOCl$_2$ (5.68 mL) was added dropwise to a solution of 4-fluoro-3-methylbenzoic acid (10 g) in MeOH (150 mL) at 0° C. over a period of 10 mins. under N$_2$. The resulting mixture was stirred at r.t. for 24 h and then the solvent was removed by evaporation. The residue was dissolved in EtOAc, washed with sat. NaHCO$_3$, sat. brine, dried and then concentrated by evaporation to afford the subtitle compound (9.85 g); $^1$H NMR: 7.93-7.83 (m, 2H), 7.04 (dd, 1H), 3.90 (s, 3H), 2.31 (s, 3H).

(ii) Methyl 3-((2-amino-4-methyl-6-(pentylamino)pyrimidin-5-yl)methyl)-4-fluorobenzoate The title compound was prepared using the product from step (i) (12.8 g) and the method of Example 12 steps (i)-(iv) to give a colourless solid (0.27 g); $^1$H NMR: 7.89-7.81 (m, 1H), 7.46 (dd, 1H), 7.32 (dd, 1H), 6.31 (t, 1H), 5.74 (s, 2H), 3.78 (s, 3H), 3.77 (s, 2H), 3.27-3.22 (m, 2H), 1.95 (s, 3H), 1.44 (qn, 2H), 1.27-1.07 (m, 4H), 0.79 (t, 3H); LC-MS m/z 361.

Example 18

Methyl 4-((2-amino-4-methyl-6-(pentylamino)pyrimidin-5-yl)methyl)-3-fluorobenzoate

(i) Methyl 4-(bromomethyl)-3-fluorobenzoate

The subtitle compound was prepared from 3-fluoro-4-methylbenzoic acid (15 g) by the method of Example 17 step (i) to give the product (14.5 g) as an orange oil; $^1$H NMR: 7.70 (dd, 1H), 7.62 (dd, 1H), 7.45 (dd, 1H), 3.85 (s, 3H), 2.31 (d, 3H).

(ii) Methyl 4-((2-amino-4-methyl-6-(pentylamino)pyrimidin-5-yl)methyl)-3-fluorobenzoate The title compound was prepared using the product from step (i) (12.8 g) and the method of Example 12 steps (i)-(iv) to give a colourless solid (40 mg); $^1$H NMR: 7.70-7.63 (m, 2H), 6.97 (dd, 1H), 6.53-6.41 (m, 1H), 6.00 (s, 2H), 3.84 (s, 3H), 3.81 (s, 2H), 3.28-3.21 (m, 2H), 1.97 (s, 3H), 1.44 (qn, 2H), 1.29-1.07 (m, 4H), 0.81 (t, 3H); LC-MS m/z 361.

Example 19

5-(2-Methoxybenzyl)-6-methyl-N4-pentylpyrimidine-2,4-diamine

The title compound was prepared by the method of Example 1 from 2-methoxy-benzaldehyde (10 g) to give the product as a light brown solid (0.74 g); $^1$H NMR: 7.19 (1H, td), 7.00 (1H, d), 6.86-6.73 (2H, m), 6.03-5.90 (1H, m), 5.76 (2H, s), 3.86 (3H, s), 3.65 (2H, s), 3.29-3.16 (2H, m), 2.02 (3H, s), 1.51-1.39 (2H, m), 1.31-1.12 (4H, m), 0.84 (3H, t); LC-MS m/z 315.

Example 20

2-((2-Amino-4-methyl-6-(pentylamino)pyrimidin-5-yl)methyl)phenol

Prepared by the method of Example 2 using the product of Example 19 (0.6 g) to give the product as a colourless solid (0.52 g); $^1$H NMR: 11.87 (1H, s), 7.89 (1H, t), 7.34 (2H, s), 7.05 (1H, t), 6.88-6.78 (2H, m), 6.74-6.68 (1H, m), 3.67 (2H, s), 3.37 (2H, q), 2.20 (3H, s), 1.49 (2H, qn), 1.29-1.11 (4H, m), 0.82 (3H, t); LC-MS m/z 301.

Example 21

5-(2-Ethoxybenzyl)-6-methyl-N$^4$-pentylpyrimidine-2,4-diamine

A suspension of the product of Example 20 (0.1 g) and $Cs_2CO_3$ (0.5 g) in DMF (2 mL) was stirred for 30 mins. Bromoethane (0.03 mL) was then added and the resulting suspension was heated at 80° C. for 1 h. The mixture was then cooled, filtered and EtOAc (10 mL) and water (5 mL) were added. The organic phase was separated, dried and concentrated to give a crude product which was purified by RPHPLC to give the title compound as a colourless solid (27 mg); $^1$H NMR: 7.13 (1H, td), 6.96 (1H, d), 6.82-6.74 (2H, m), 5.93 (1H, t), 5.62 (2H, s), 4.09 (2H, q), 3.62 (2H, s), 3.23 (2H, q), 1.99 (3H, s), 1.41 (2H, qn), 1.39 (3H, t), 1.28-1.08 (4H, m), 0.82 (3H, t); LC-MS m/z 329.

Example 22

5-(2-(3-(Dimethylamino)propoxy)benzyl)-6-methyl-N-pentyl-pyrimidine-2,4-diamine The title compound was prepared by the method of Example 3 using the product of Example 20 (0.1 g) and N,N-dimethylaminopropylchloride hydrochloride (0.105 g) to give a colourless solid (27 mg); $^1$H NMR: 7.14 (1H, td), 6.96 (1H, d), 6.81-6.74 (2H, m), 5.92 (1H, t), 5.63 (2H, s), 4.05 (2H, t), 3.63 (2H, s), 3.23 (2H, q), 2.41 (2H, t), 2.15 (6H, s), 1.99 (3H, s), 1.90 (2H, qn), 1.42 (2H, qn), 1.28-1.17 (2H, m), 1.17-1.07 (2H, m), 0.81 (3H, t); LC-MS m/z 386.

Example 23

5-(3-Methoxybenzyl)-6-methyl-N4-pentylpyrimidine-2,4-diamine

The title compound was prepared by the method of Example 1 from 3-methoxy-benzaldehyde (10 g) to give a light brown solid (3.7 g); $^1$H NMR: 7.16 (1H, dd), 6.75-6.66 (3H, m), 6.30 (1H, s), 5.82 (2H, s), 3.72 (2H, s), 3.70 (3H, s), 3.30-3.23 (2H, m), 2.03 (3H, s), 1.49-1.39 (2H, m), 1.29-1.08 (4H, m), 0.82 (3H, t); LC-MS m/z 315.

Example 24

3-((2-Amino-4-methyl-6-(pentylamino)pyrimidin-5-yl)methyl)phenol

The title compound was prepared by the method of Example 2 using the product of Example 23 (0.9 g) to give a light brown solid (0.72 g); $^1$H NMR: 9.25 (1H, s), 7.20-6.93 (2H, m), 6.65 (2H, s), 6.60-6.53 (1H, m), 6.50 (1H, s), 3.71 (2H, s), 3.43-3.20 (2H, m), 2.10 (3H, s), 1.46 (2H, qn), 1.31-1.06 (4H, m), 0.82 (3H, t); LC-MS m/z 301.

Example 25

5-(3-(3-(Dimethylamino)propoxy)benzyl)-6-methyl-N-pentyl-pyrimidine-2,4-diamine The title compound was prepared by the method of Example 3 using the product of Example 24 (0.1 g) and N,N-dimethylaminopropylchloride hydrochloride (0.105 g) to give a colourless solid (0.054 g); $^1$H NMR: 7.14 (1H, dd), 6.72-6.64 (3H, m), 6.10 (1H, t), 5.63 (2H, s), 3.92 (2H, t), 3.69 (2H, s), 3.25 (2H, q), 2.31 (2H, t), 2.12 (6H, s), 2.01 (3H, s), 1.80 (2H, qn), 1.43 (2H, qn), 1.28-1.19 (2H, m), 1.18-1.09 (2H, m), 0.82 (3H, t); LC-MS m/z 386.

Example 26

6-Methyl-N$^4$-pentyl-5-(3-(2-(piperidin-1-yl)ethoxy)benzyl)pyrimidine-2,4-diamine The title compound was prepared by the method of Example 3 using the product of Example 24 (0.1 g) and N-2-chloroethylpiperidinehydrochloride (0.122 g) to give a colourless oil (0.045 g); $^1$H NMR: 7.14 (1H, dd), 6.74-6.65 (3H, m), 6.09 (1H, t), 5.63 (2H, s), 3.98 (2H, t), 3.69 (2H, s), 3.24 (2H, q), 2.60 (2H, t), 2.42-2.37 (4H, m), 2.01 (3H, s), 1.51-1.33 (8H, m), 1.27-1.19 (2H, m), 1.17-1.10 (2H, m), 0.81 (3H, t); LC-MS m/z 412.

Example 27

5-(3-(2-(Dimethylamino)ethoxy)benzyl)-6-methyl-N$^4$-pentylpyrimidine-2,4-diamine The title compound was prepared by the method of Example 3 using the product of Example 24 (0.1 g) and N-2-dimethylaminochloride hydrochloride (0.096 g) to give a light brown solid (0.022 g); $^1$H NMR: 7.15 (1H, dd), 6.72 (1H, d), 6.69-6.65 (2H, m), 6.10 (1H, t), 5.63 (2H, s), 3.97 (2H, t), 3.69 (2H, s), 3.25 (2H, q), 2.58 (2H, t), 2.19 (6H, s), 2.01 (3H, s), 1.43 (2H, qn), 1.29-1.09 (4H, m), 0.82 (3H, t); LC-MS m/z 372.

Example 28

6-Methyl-N$^4$-pentyl-5-(3-(2-(pyrrolidin-1-yl)ethoxy)benzyl)pyrimidine-2,4-diamine The title compound was prepared by the method of Example 3 using the product of Example 24 (0.1 g) and N-2-chloroethylpyrrolidine hydrochloride (0.115 g) to give a colourless oil (0.036 g); $^1$H NMR: 7.15 (1H, dd), 6.74-6.65 (3H, m), 6.11 (1H, s), 5.65 (2H, s), 3.99 (2H, t), 3.70 (2H, s), 3.27-3.22 (2H, m), 2.74 (2H, t), 2.44-2.36 (4H, m), 2.02 (3H, s), 1.71-1.63 (4H, m), 1.44 (2H, qn), 1.30-1.19 (2H, m), 1.18-1.10 (2H, m), 0.82 (3H, t); LC-MS m/z 398.

Example 29

5-(3-((Dimethylamino)methyl)benzyl)-6-methyl-N$^4$-pentylpyrimidine-2,4-diamine (i) Ethyl 2-(3-((2-amino-4-methyl-6-(pentylamino)pyrimidin-5-yl)methyl)phenyl)acetate The method of Example 12 using methyl 3-bromomethylbenzoate (6 g) was used to provide the subtitle compound as an orange oil which solidified on standing (0.7 g); $^1$H NMR: 7.79-7.71 (2H, m), 7.45-7.32 (2H, m), 6.36 (1H, s), 5.78 (2H, s), 4.29 (2H, q), 3.82 (2H, s), 3.29-3.22 (2H, m), 2.01 (3H, s), 1.49-1.38 (2H, m), 1.28-1.07 (7H, m), 0.79 (3H, t).

(ii) (3-((2-Amino-4-methyl-6-(pentylamino)pyrimidin-5-yl)methyl)phenyl)methanol

A solution of the product of step (i) (0.21 g) in THF (2 mL) was added to a solution of LiAlH$_4$ (1M in THF, 0.88 mL) in THF (2 mL) at 0° C. The mixture was stirred at r.t. for 2 h. A further portion of LiAlH$_4$ (0.88 mL) was then added and the mixture was stirred at r.t. for 15 h. The mixture was then poured cautiously into 2M NaOH (20 mL) and the aqueous phase was extracted with EtOAc (3×20 mL). The combined organic phase was dried and concentrated by evaporation to give the subtitle compound as a colourless solid which was used without further purification (0.176 g); $^1$H NMR: 7.19 (1H, dd), 7.09 (2H, d), 7.07 (2H, s), 6.97 (1H, d), 6.12 (1H, t), 5.10 (1H, t), 4.43 (2H, d), 3.72 (2H, s), 3.24 (2H, q), 2.01 (3H, s), 1.44 (2H, qn), 1.28-1.10 (4H, m), 0.82 (3H, t).

(iii) 5-(3-(Chloromethyl)benzyl)-6-methyl-N$^4$-pentylpyrimidine-2,4-diamine

SOCl$_2$ (0.049 mL) was added to a stirred solution of the product from step (ii) (0.176 g) in DCM (5 mL) at r.t. The mixture was stirred for 1 h, then the solvent was removed to give the subtitle compound as a yellow oil that was used without further purification (0.182 g); $^1$H NMR: 7.97 (1H, t), 7.34-7.25 (3H, m), 7.21 (2H, s), 7.15-7.09 (1H, m), 4.72 (2H, s), 3.86 (2H, s), 3.37 (2H, q), 2.19 (3H, s), 1.47 (2H, qn), 1.27-1.17 (2H, m), 1.15-1.06 (2H, m), 0.80 (3H, t).

(iv) 5-(3-((Dimethylamino)methyl)benzyl)-6-methyl-N$^4$-pentylpyrimidine-2,4-diamine 2M Dimethylamine solution in EtOH (0.4 mL) was added to a solution of the product of step (iii) (0.09 g) in DMF (2 mL) and the mixture was stirred at r.t. for 15 h. Sat NaHCO$_3$ was then added and the aqueous phase was extracted with EtOAc (2×10 mL). The combined organic phases were washed with water (3×5 mL), dried and concentrated to a residue which was purified by RPHPLC to give the title compound as an off white solid (44 mg); $^1$H NMR: 7.19 (1H, dd), 7.07-7.03 (2H, m), 6.98 (1H, d), 6.13 (1H, s), 5.63 (2H, s), 3.72 (2H, s), 3.29 (2H, s), 3.24 (2H, q), 2.10 (6H, s), 2.00 (3H, s), 1.43 (2H, qn), 1.27-1.20 (2H, m), 1.18-1.10 (2H, m), 0.82 (3H, t); LC-MS m/z 342.

Example 30

5-(4-(3-(Dimethylamino)prop-1-ynyl)benzyl)-6-methyl-N4-pentyl-pyrimidine-2,4-diamine (i) 5-(4-Iodobenzyl)-6-methyl-N$^4$-pentylpyrimidine-2,4-diamine The method of Example 12 using 4-iodobenzylbromide and ethylacetoacetate was used to provide the subtitle compound as a solid (60 mg); $^1$H NMR: 7.59 (2H, d), 6.91 (2H, d), 6.16-6.09 (1H, m), 5.69-5.63 (2H, m), 3.69 (2H, s), 3.27-3.18 (2H, m), 1.99 (3H, s), 1.46-1.37 (2H, m), 1.28-1.06 (4H, m), 0.82 (3H, t); LC-MS m/z 411.

(ii) 5-(4-(3-(Dimethylamino)prop-1-ynyl)benzyl)-6-methyl-N$^4$-pentylpyrimidine-2,4-diamine 1-Dimethylamino-2-propyne (24 mg) was dissolved in THF (2 mL) purged with nitrogen and CuI (4.64 mg) was added. The mixture was stirred for 30 mins. and added to a suspension of the product of step (i) (0.1 g) and Pd(PPh$_3$)$_4$ (14.08 mg) in a 1:1 mixture of THF and triethylamine (2 mL). The reaction mixture was then heated to 100° C. for 16 h, cooled and concentrated by evaporation. The residue was purified by RPHPLC to give the title compound as a solid (9 mg); $^1$H NMR: 7.31 (2H, d), 7.09 (2H, d), 6.16-6.11 (1H, m), 5.65 (2H, s), 3.74 (2H, s), 3.41 (2H, s), 2.22 (6H, s), 2.00 (3H, s), 1.46-1.40 (2H, m), 1.27-1.16 (4H, m), 1.14-1.06 (2H, m), 0.81 (3H, t); LC-MS m/z 366.

Example 31

5-(4-(3-(Dimethylamino)propyl)benzyl)-6-methyl-N$^4$-pentylpyrimidine-2,4-diamine The product of Example 30 (8 mg) was dissolved in EtOH and hydrogenated in a H-cube™ hydrogenator using a 10% Pt/C reaction cartridge (available from ThalesNano Nanotechnology, Hungary) using the "full H$_2$ mode". The solvent was removed by evaporation and the resulting residue was purified via RPHPLC to give the title compound as a solid (1 mg); $^1$H NMR: 7.06 (2H, d), 7.00 (2H, d), 6.09-6.03 (1H, m), 5.62 (2H, s), 3.68 (2H, s), 3.25-3.19 (2H, m), 2.19-2.13 (2H, m), 2.09 (6H, s), 2.00 (3H, s), 1.66-1.59 (2H, m), 1.46-1.38 (2H, m), 1.25-1.17 (4H, m), 1.16-1.08 (2H, m), 0.81 (3H, t); LC-MS m/z 370.

Example 32

5-(3-(3-(Dimethylamino)propyl)benzyl)-6-methyl-N$^4$-pentylpyrimidine-2,4-diamine (i) 5-(3-(3-(Dimethylamino)prop-1-ynyl)benzyl)-6-methyl-N$^4$-pentylpyrimidine-2,4-diamine The method of Example 30 using 3-iodobenzyl bromide was used to provide the subtitle compound (60 mg); LC-MS m/z 366.

(ii) 5-(3-(3-(Dimethylamino)propyl)benzyl)-6-methyl-N$^4$-pentylpyrimidine-2,4-diamine The method of Example 31 using the product from step (i) (0.06 g) was used to provide the subtitle compound as a solid (8 mg); $^1$H NMR: 7.15 (1H, t), 7.00-6.89 (3H, m), 6.12-6.06 (1H, m), 5.62 (2H, s), 3.70 (2H, s), 3.29 (2H, s), 3.28-3.21 (2H, m), 2.18-2.13 (2H, m), 2.08 (6H, s), 2.01 (3H, s), 1.69-1.57 (2H, m), 1.49-1.38 (2H, m), 1.27-1.18 (2H, m), 1.18-1.07 (2H, m), 0.82 (3H, t); LC-MS m/z 370.

Example 33

5-(4-(3-(Dimethylamino)propoxy)-2-methylbenzyl)-6-methyl-N$^4$-pentylpyrimidine-2,4-diamine (i) 5-(4-Methoxy-2-methylbenzyl)-6-methyl-N$^4$-pentylpyrimidine-2,4-diamine The method of Example 1 using 4-methoxy-2-methylbenzaldehyde (10 g) was used to provide the subtitle compound as a cream solid (0.67 g); $^1$H NMR: 6.77 (d, 1H), 6.59 (dd, 1H), 6.49 (d, 1H), 5.97 (t, 1H), 5.63 (s, 2H), 3.68 (s, 3H), 3.52 (s, 2H), 3.22 (q, 2H), 2.32 (s, 3H), 1.90 (s, 3H), 1.42 (qn, 2H), 1.29-1.09 (m, 4H), 0.82 (t, 3H).

(ii) 4-((2-Amino-4-(pentylamino)pyrimidin-5-yl) methyl)-3-methylphenol

The method of Example 2 using the product of step (i) (0.5 g) was used to provide the subtitle compound as a colourless solid that was used without purification (0.350 g); $^1$H NMR: 8.96 (s, 1H), 6.58 (s, 1H), 6.48-6.30 (m, 2H), 5.95 (s, 1H), 5.62 (s, 2H), 3.48 (s, 2H), 3.22 (q, 2H), 2.25 (s, 3H), 1.90 (s, 3H), 1.41 (qn, 2H), 1.28-1.09 (m, 4H), 0.82 (t, 3H); LC-MS m/z 313 (multimode −).

(iii) 5-(4-(3-(Dimethylamino)propoxy)-2-methylbenzyl)-6-methyl-N$^4$-pentylpyrimidine-2,4-diamine The method of Example 3 using the product of step (ii) (0.1 g) and dimethylaminopropyl-chloride hydrochloride (0.075 g) was used to provide the title compound as a colourless solid (13 mg); $^1$H NMR: 6.76 (d, 1H), 6.57 (dd, 1H), 6.47 (d, 1H), 5.97 (t, 1H), 5.63 (s, 2H), 3.91 (t, 2H), 3.52 (s, 2H), 3.22 (q, 2H), 2.34-2.27 (m, 5H), 2.12 (s, 6H), 1.90 (s, 3H), 1.79 (qn, 2H), 1.46-1.36 (m, 2H), 1.27-1.06 (m, 4H), 0.81 (t, 3H); LC-MS m/z 400.

Example 34

(R)-Methyl 2-(3-(1-(2-amino-5-(4-(3-(dimethylamino)propoxy)benzyl)-6-methylpyrimidin-4-ylamino)-3-hydroxypropyl)phenyl)acetate

(i) 4-((2-Amino-4-bromo-6-methylpyrimidin-5-yl)methyl)phenol and 4-((2-amino-4-chloro-6-methylpyrimidin-5-yl)methyl)phenol A solution of BBr$_3$ (1M in DCM, 15.2 mL) was added portion-wise to a stirred suspension to the product of Example 1 step (iii) (1 g) in DCM (20 mL) at 0° C., over a period of 10 mins. under N$_2$. The resulting mixture was stirred at 0° C. for 1 h. The mixture was then diluted with 2M HCl (30 mL) and MeOH (10 mL) then stirred at r.t. for 30 mins. The organic phase was separated and the aqueous phase was extracted with EtOAc (2×50 mL). The combined organic extracts were dried and concentrated by evaporation to afford a 1:1 mixture of the subtitle compounds (0.230 g) which were used in the subsequent step without purification; $^1$H NMR: 6.90 (4H, d), 6.67 (4H, d), 3.89-3.79 (4H, m), 2.22 (3H, s), 2.20 (3H, s).

(ii) 4-Bromo-5-(4-(3-(dimethylamino)propoxy)benzyl)-6-methylpyrimidin-2-amine and 4-Chloro-5-(4-(3-(dimethylamino)propoxy)benzyl)-6-methylpyrimidin-2-amine 3-(Dimethylamino)propyl chloride hydrochloride (0.437 g) was added to a stirred suspension of the product of step (i) (0.23 g), Cs$_2$CO$_3$ (2.401 g) and NaI (0.069 g) in DMF (10 mL). The resulting suspension was stirred at 80° C. for 3 h., cooled, and diluted with EtOAc (20 mL). The organic phase was washed with water (3×30 mL), brine (30 mL) dried and concentrated by evaporation. The crude product was purified by FCC eluting with DCM then 10:2 DCM-McOH to afford a 1:1 mixture of the subtitle compounds (0.043 g) which were used in the subsequent step without purification; $^1$H NMR: 7.00 (d, 4H), 6.88-6.79 (m, 4H), 3.94 (t, 4H), 3.89 (s, 2H), 3.87 (s, 2H), 2.41 (t, 4H), 2.19 (s, 18H), 1.84 (qn, 4H).

(iii) (E)-tert-Butyl 3-(3-(hydroxymethyl)phenyl) acrylate

A mixture of (3-bromophenyl)methanol (7.3 g), tert-butyl acrylate (15 g), palladium acetate (0.235 g) and tri(o-tolyl) phosphine (1.25 g) in MeCN (80 mL) was heated at 90° C. for 2 h. The solution was then cooled, concentrated by evaporation. The resulting residue was dissolved in EtOAc, washed with water, dried and concentrated by evaporation. The crude product was purified by FCC eluting with using 8:2 to 7:3 isohexane-EtOAc to give the subtitle compound (7.8 g); $^1$H NMR (CDCl$_3$): 7.58 (1H, d), 7.52 (1H, s), 7.45-7.33 (3H, m), 6.38 (1H, d), 4.72 (2H, s), 1.53 (9H, s).

(iv) (R)-tert-Butyl 3-(benzyl((S)-1-phenylethyl) amino)-3-(3-((tert-butyldimethyl-silyloxy)methyl) phenyl)propanoate A solution of butyl lithium (2.5 M in hexane, 34 mL) was added to a solution of (S)-(−)-N-benzyl-α-methylbenzylamine in THF (200 mL) at −78° C. and the mixture was stirred for 45 mins. A solution of the product of step (iii) (7.8 g) in THF (20 mL) was added and stirring was continued for 3 h. Then the cooling bath was removed, NH$_4$Cl solution was added and the solution was allowed to warm to r.t. EtOAc and water were added, the organic phase was separated, dried and concentrated to give a residue which was passed through silica gel eluting with 4:1 isohexane-EtOAc. Removal of solvent by evaporation gave a residue which was dissolved in DMF (120 mL). Imidazole (5 g) and tert-butyl-dimethylsilylchloride were added and the solution was stirred at r.t. for 2 h. EtOAc and water were then added, the organic phase was separated, dried and concentrated to give the crude product which was purified by FCC eluting with 95:5 isohexane-EtOAc to give the subtitle compound (18 g); LC-MS m/z 560 (APCI+).

(v) (R)-3-(Benzyl((S)-1-phenylethyl)amino)-3-(3-((tert-butyldimethylsilyloxy)-methyl)phenyl)propan-1-ol The product of step (iv) (18 g) was dissolved in THF (120 mL) and a solution of LiAlH$_4$ (1M in THF, 45 mL) was added. The mixture was then stirred at r.t. for 4 h. and then water was added. 45% NaOH solution and water were added and the mixture stirred for 1 h. The solvent was then removed by decantation to give a residue which was dissolved in diethyl ether. The organic solution was washed with brine, dried and concentrated by evaporation to give the subtitle compound (15.5 g); LC-MS m/z 490 (APCI+).

(vi) (3-((R)-1-(Benzyl((S)-1-phenylethyl)amino)-3 (methoxymethoxy)propyl)-phenyl)methanol To a solution of the product from step (v) and DIPEA (17 mL) in DCM (160 mL) at 0° C. was added chloromethyl methylether. The mixture was warmed to r.t. and stirred for 18 h. A further aliquot of chloromethyl methylether (0.4 mL) was added and the mixture further stirred for 18 h. The mixture was washed with water, dried and concentrated by evaporation. The resulting residue was dissolved in THF (250 mL). Tetrabutylammonium fluoride solution (75 wt % in water, 10 mL) was added and the mixture stirred for 4 h. Brine and EtOAc were added, the organic phase was separated, washed with brine, dried and concentrated by evaporation to give the crude product which was purified by FCC eluting with 7:3 isohexane-EtOAc to give the subtitle compound (10.9 g); $^1$H NMR (CDCl$_3$): 7.45-7.18 (10H, m), 4.71 (2H, d), 4.42 (2H, s), 4.15-4.08 (1H, m), 3.98-3.94 (1H, m), 3.84-3.64 (2H, m), 3.28-3.22 (5H, m), 2.20-2.10 (1H, m), 1.90-1.78 (1H, m), 1.69 (1H bs), 1.16 (3H, d).

(vii) 3-((R)-1-(Benzyl((S)-1-phenylethyl)amino)-3-(methoxymethoxy)propyl)benzyl methanesulfonate Methane sulphonyl chloride (1.912 mL) was added dropwise to a solution of the product from step (vi) (9.5 g) and triethylamine (4.8 mL) in DCM (100 mL) at 0-5° C. under N$_2$. The resulting mixture was stirred for 1 h, then the solvent was removed to give the crude subtitle compound which was used in the next step without further purification (11.27 g); LC-MS m/z 498 (APCI+)

(viii) 2-(3-((R)-1-(Benzyl((S)-1-phenylethyl)amino)-3-(methoxymethoxy)propyl)-phenyl)acetonitrile KCN (6 g) was added in one portion to the product of step (vii) (11.27 g) in DMSO (30 mL) and DMF (30 mL) and the mixture was warmed to 50° C. under N$_2$. The resulting mixture was stirred at 50° C. for 18 h then partitioned between EtOAc and water. The organic phase was separated, washed with water, dried and concentrated by evaporation to give the crude subtitle compound which was used in the next step without further purification (7.69 g); LC-MS m/z 429 (APCI+).

(ix) Methyl 2-(3-((R)-1-(benzyl((S)-1-phenylethyl)amino)-3-hydroxypropyl)phenyl)acetate A solution of KOH (2.81 g) dissolved in water (10 mL) was added to a stirred solution of the product of step (viii) (7.69 g, 17.94 mmol) in EtOH (50 mL) at r.t. The mixture was stirred at reflux for 24 h. The mixture was then concentrated by evaporation and the resulting residue azeotroped with toluene. MeOH (100 mL) followed by conc. HCl (3 mL) were added to the residue and the mixture was stirred at r.t. for 3 days. The mixture was then concentrated by evaporation and the resulting residue was partitioned between EtOAc and water. The organic phase was separated, washed with water, dried and concentrated by evaporation. The crude product was purified by FCC eluting with 7:3 isohexane-EtOAc to afford the subtitle compound as an oil (2.32 g); $^1$H NMR (CDCl$_3$): 7.43-7.19 (m, 14H); 4.14-4.08 (m, 1H); 3.96-3.92 (m, 2H); 3.70 (s, 3H); 3.66 (s, 2H); 3.62-3.53 (m, 2H); 3.41-3.35 (m, 1H); 2.24-2.15 (m, 1H); 1.84 (br s, 1H); 1.74-1.65 (m, 1H); 1.04 (d, 3H); LC-MS m/z 418 (APCI+).

(x) (R)-methyl 2-(3-(1-amino-3-hydroxypropyl)phenyl)acetate

A suspension of the product of step (ix) (2.3 g) and Pd/C (0.9 g) in MeOH (60 mL) was stirred under a H$_2$ pressure of 45 psi at r.t. for 24 h. The mixture was then filtered through diatomaceous earth (Celite™) and the solvent was evaporated to give a residue which was purified by FCC eluting with 84:16 DCM-McOH to give the subtitle compound as an oil (480 mg); $^1$H NMR: 7.26-7.07 (m, 4H); 3.89 (t, 1H); 3.64 (s, 2H); 3.61 (s, 3H); 3.47-3.37 (m, 2H); 1.71-1.60 (m, 2H).

(xi) (R)-methyl 2-(3-(1-(2-amino-5-(4-(3-(dimethylamino)propoxy)benzyl)-6-methylpyrimidin-4-ylamino)-3-hydroxypropyl)phenyl)acetate A solution of the products of step (ii) (0.045 g) and the product of step (x) (0.107 g) in butan-1-ol (3 mL) were sealed into a microwave tube and heated to 170° C. in a microwave reactor for 2.5 h. The solvent was then removed by evaporation and the resulting residue was partitioned between EtOAc (5 mL) and water (5 mL). The organic phase was separated and the aqueous phase was extracted with EtOAc (5 mL). The combined organic phases were dried and concentrated by evaporation to give a residue which was purified by RPHPLC to give the title compound as a colourless gum (11 mg); $^1$H NMR: 7.20-7.13 (m, 1H), 7.10-7.00 (m, 5H), 6.82 (d, 2H), 6.41 (d, 1H), 5.60 (s, 2H), 5.36-5.26 (m, 1H), 4.52 (t, 1H), 3.94 (t, 2H), 3.78 (d, 1H), 3.69 (d, 1H), 3.60 (s, 3H), 3.57 (s, 4H), 2.37-2.31 (m, 2H), 2.14 (s, 6H), 2.02 (s, 3H), 1.91-1.77 (m, 4H); LC-MS m/z 522.

Example 35

(R)-Methyl 2-(3-(1-(2-amino-5-(4-(3-(dimethylamino)propoxy)-2-methoxybenzyl)-6-methylpyrimidin-4-ylamino)-3-hydroxypropyl)phenyl)acetate (R)-Methyl 2-(3-(1-(2-amino-5-(4-(3-(dimethylamino)propoxy)-2-methoxybenzyl)-6-methylpyrimidin-4-ylamino)-3-hydroxypropyl)phenyl)acetate A solution of the product of Example 11 step (v) (0.15 g) and the product of Example 34 step (x) (0.184 g) in butan-1-ol (3 mL) were sealed into a microwave tube and heated to 170° C. in a microwave reactor for 2 h. The solvent was then removed by evaporation and the resulting residue was diluted with MeOH (2 mL) and conc. H$_2$SO$_4$ (0.5 mL). The mixture was then stirred at 65° C. for 2 h, allowed to cool, adjusted to pH 7 with sat.

NaHCO$_3$ and then extracted EtOAc (3×10 mL). The combined organic phases were dried and concentrated by evaporation to give a crude product which was purified by RPHPLC to give the title compound as a colourless solid (43.0 mg); $^1$H NMR: 7.16 (1H, dd), 7.09-7.00 (2H, m), 6.67 (1H, d), 6.55 (1H, d), 6.40 (1H, dd), 6.21 (1H, d), 5.58 (2H, s), 5.32-5.24 (1H, m), 4.47 (1H, s), 3.96 (2H, t), 3.82 (3H, s), 3.65-3.55 (9H, m), 2.34 (2H, t), 2.14 (6H, s), 2.01 (3H, s), 1.87-1.77 (4H, m); LC-MS m/z 552.

Example 36

3-(4-((2-Amino-4-methyl-6-(pentylamino)pyrimidin-5-yl)methyl)-3-methoxyphenoxy)propan-1-ol (i) 4-(3-(tert-Butyldimethylsilyloxy)propoxy)-2-methoxybenzaldehyde (3-Bromopropoxy)(tert-butyl)dimethylsilane (6.85 mL) and K$_2$CO$_3$ (4.09 g, 29.6 mmol) were added to a solution of 4-hydroxy-2-methoxybenzaldehyde (3.00 g) in DMF (30 mL) and the mixture was stirred for 14 h at r.t. Brine was added, and the mixture was then extracted twice with EtOAc. The combined organic layers were washed with water and brine, dried (MgSO$_4$) and concentrated. The resulting residue was purified by FCC to give the subtitle compound as colourless oil (5.97 g); $^1$H NMR (CDCl$_3$):

10.29 (1H, s), 7.80 (1H, d), 6.55 (1H, dd), 6.45 (1H, d), 4.15 (2H, t), 3.90 (3H, s), 3.81 (2H, t), 2.00 (2H, tt), 0.89 (9H, s), 0.05 (6H, s).

(ii) (4-(3-(tert-Butyldimethylsilyloxy)propoxy)-2-methoxyphenyl)methanol

NaBH$_4$ (0.35 g) was added to a solution of the product of step (i) (5.97 g) in THF/MeOH (30 mL/3 mL) at 0° C., and then the mixture was stirred for 1 h. The reaction was quenched with brine, and extracted twice with EtOAc. The combined organic layers were washed with brine, dried (MgSO$_4$) and concentrated. The residue was purified by FCC to give subtitle compound as colourless oil (5.76 g); $^1$H NMR (CDCl$_3$): 7.14 (1H, d), 6.46 (2H, m), 4.61 (2H, s), 4.06 (2H, t), 3.85 (3H, s), 3.81 (2H, t), 2.15 (1H, br s), 1.99 (2H, tt), 0.89 (9H, s), 0.05 (6H, s).

(iii) Methyl 2-(4-(3-(tert-butyldimethylsilyloxy)propoxy)-2-methoxybenzyl)-3-oxobutanoate Methanesulfonyl chloride (0.93 mL) was added to the mixture of the product from step (ii) (2.50 g) and DIPEA (2.09 mL) in THF (30 mL) at r.t. and the mixture was stirred for 2 h. The resulting solid was removed by filtration. The filtrate was concentrated in vacuo, and then dissolved in DMF (20 mL). Methyl acetoacetate (0.99 mL) was added to a suspension of NaH (55% oil dispersion, 0.37 g) in DMF (15 mL) at 0° C. and the mixture was stirred for 15 min. The DMF solution described above and KI (1.27 g) were added to the mixture and it was all stirred at 80° C. for 4 h. The mixture was cooled to r.t. and diluted with EtOAc. The mixture was then washed with sat. NaHCO$_3$ and brine. The organic layer was dried (MgSO$_4$) and concentrated. The resulting residue was purified by FCC to give the subtitle compound as colourless oil (1.80 g); $^1$H NMR (CDCl$_3$): 6.99 (1H, d), 6.42 (1H, d), 6.38 (1H, dd), 4.03 (2H, t), 3.89 (1H, t), 3.81 (3H, s), 3.80 (2H, t), 3.67 (3H, s), 3.09 (2H, m), 2.17 (3H, s), 1.97 (2H, tt), 0.88 (9H, s), 0.04 (6H, s).

(iv) 2-Amino-5-(4-(3-(tert-butyldimethylsilyloxy)propoxy)-2-methoxybenzyl)-6-methylpyrimidin-4-ol Guanidium carbonate (0.98 g) was added to a solution of the product from step (iii) (1.78 g) in MeOH (50 mL) and the mixture was heated at 65° C. for 7 h. The mixture was then cooled to r.t. and water (50 mL) was added. The resulting solid was collected by filtration and washed with EtOH/water (50 mL/50 mL), water (50 mL), EtOH (50 mL) to afford subtitle compound as a white solid (1.53 g); $^1$H NMR: 6.71 (1H, d), 6.41 (1H, d), 6.37 (1H, dd), 6.32 (2H, br s), 3.97 (2H, t), 3.79 (3H, s), 3.75 (2H, t), 3.45 (2H, s), 1.92 (3H, s), 1.85 (2H, tt), 0.85 (9H, s), 0.02 (6H, s); LC-MS m/z 433 ESI.

(v) 2-Amino-5-(4-(3-(tert-butyldimethylsilyloxy)propoxy)-2-methoxybenzyl)-6-methylpyrimidin-4-yl 2,4,6-trimethylbenzenesulfonate N$^1$,N$^1$,N$^3$,N$^3$-tetramethylpropane-1,3-diamine (0.88 mL) and 2,4,6-trimethylbenzene-1-sulfonyl chloride (1.15 g) were added to the solution of the product from step (iv) (1.52 g) in THF (15 mL) and the mixture was stirred at r.t. After 22 h, 0.1N HCl aq. (45 mL) was added and the mixture was then extracted twice with CHCl$_3$. The organic layer was dried (MgSO$_4$) and concentrated. The resulting residue was purified by FCC to give the subtitle compound as pale yellow oil (1.92 g); $^1$H NMR (CDCl$_3$): 6.94 (2H, s), 6.71 (1H, d). 6.41 (1H, d), 6.33 (1H, dd), 4.72 (2H, br s), 4.02 (2H, t), 3.81 (2H, t), 3.79 (3H, s), 3.76 (2H, s), 2.61 (6H, s), 2.31 (3H, s), 2.26 (3H, s), 1.98 (2H, tt), 0.89 (9H, s), 0.05 (6H, s); LC-MS m/z 616 ESI.

(vi) 5-(4-(3-(tert-Butyldimethylsilyloxy)propoxy)-2-methoxybenzyl)-6-methyl-N$^4$-pentylpyrimidine-2,4-diamine Trifluoroacetic acid (0.48 mL) and amylamine (1.78 mL) were added to the solution of the product from step (v) (1.90 g) in propionitrile (19 mL) and the mixture was stirred at 100° C. for 3 h. The solvent was then removed by evaporation and the resulting residue was diluted with EtOAc (50 mL) and washed with 4% NH$_3$ solution (20 mL×4) and brine (20 mL), then dried (MgSO$_4$) and concentrated. The resulting residue was purified by FCC to give the subtitle compound as pale yellow oil (1.03 g); $^1$H NMR (CDCl$_3$): 6.82 (1H, d), 6.47 (1H, d), 6.40 (1H, dd), 5.10 (2H, br s), 4.03 (2H, t), 3.88 (3H, s), 3.79 (2H, t), 3.72 (1H, q), 3.60 (2H, s), 3.28 (2H, q), 2.36 (3H, s), 1.97 (2H, tt), 1.44 (2H, tt), 1.25 (2H, m), 1.15 (2H, m), 0.89 (9H, s), 0.86 (3H, t), 0.05 (6H, s); LC-MS m/z 502 ESI.

(vii) 3-(4-((2-Amino-4-methyl-6-(pentylamino)pyrimidin-5-yl)methyl)-3-methoxyphenoxy)propan-1-ol Tetrabutylammonium fluoride (1.0 M THF solution, 4.1 mL) was added to the solution of the product from step (vi) (1.03 g) in THF (6 mL) and the mixture was stirred at r.t. for 4 h. The mixture was then diluted with EtOAc (30 mL), and washed with 4% NH$_3$ solution (20 mL), brine (20 mL), then dried (Na$_2$SO$_4$) and concentrated. The resulting residue was purified by FCC to give the title compound as a white solid (0.51 g); $^1$H NMR (CDCl$_3$): 6.82 (1H, d), 6.48 (1H, d), 6.38 (1H, dd), 4.87 (1H, br t), 4.69 (2H, br s), 4.10 (2H, t), 3.88 (3H, s), 3.86 (2H, t), 3.61 (2H, s), 3.28 (2H, dq), 2.32 (3H, s), 2.04 (2H, tt), 1.90 (1H, br s), 1.44 (2H, tt), 1.25 (2H, m), 1.15 (2H, m), 0.84 (3H, t); LC-MS m/z 388 ESI.

Example 37

5-(2-Methoxy-4-(3-morpholinopropoxy)benzyl)-6-methyl-N$^4$-pentylpyrimidine-2,4-diamine Methanesulfonyl chloride (0.030 mL) was added to the mixture of the product from Example 36 (0.14 g) and triethylamine (0.053 mL) in THF (5 mL) at 0° C. The resulting mixture was stirred for 30 min. Sat. NaHCO$_3$ was then added and then the solution was extracted twice with CHCl$_3$. The organic layer was dried (MgSO$_4$) and concentrated. The resulting residue was dissolved in DMF (5 mL). Morpholine (0.33 mL) was added and the mixture was stirred at 60° C. for 5 h. 4% NH$_3$ solution was then added and brine and the mixture was extracted twice with EtOAc. The combined organic layers were washed twice with brine, dried (Na$_2$SO$_4$) and concentrated. The resulting residue was purified by FCC to give the title compound as a white solid (0.13 g); $^1$H NMR: 6.59 (1H, d), 6.52 (1H, d), 6.37 (1H, dd), 5.89 (1H, br t), 5.65 (2H, br s), 3.94 (2H, t), 3.82 (3H, s), 3.55 (4H, t), 3.51 (2H, s), 3.20 (2H, q), 2.39 (2H, t), 2.34 (4H, m), 1.98 (3H, s), 1.83 (2H, tt), 1.41 (2H, tt), 1.24 (2H, m), 1.14 (2H, m), 0.84 (3H, t); LC-MS m/z 457 ESI.

Example 38

5-(2-Methoxy-4-(3-(4-methylpiperazin-1-yl)propoxy)benzyl)-6-methyl-$N^4$-pentylpyrimidine-2,4-diamine The title compound was prepared by the method of Example 37 using the product from Example 36 (0.14 g) as a white solid (0.13 g); $^1$H NMR: 6.59 (1H, d), 6.52 (1H, d), 6.37 (1H, dd), 5.88 (1H, br t), 5.64 (2H, br s), 3.93 (2H, t), 3.82 (3H, s), 3.51 (2H, s), 3.21 (2H, q), 2.36 (2H, t), 2.29 (8H, m), 2.12 (3H, s), 1.98 (3H, s), 1.82 (2H, tt), 1.41 (2H, tt), 1.24 (2H, m), 1.14 (2H, m), 0.82 (3H, t); LC-MS m/z 470 ESI.

Example 39

5-(4-(4-(Dimethylamino)butyl)-2-methoxybenzyl)-6-methyl-$N^4$-pentylpyrimidine-2,4-diamine

(i) Methyl 4-(4-(tert-butyldimethylsilyloxy)but-1-ynyl)-2-methoxybenzoate 4-(tert-Butyldimethylsiloxy)butyne (3.7 g) and methyl 4-bromo-2-methoxybenzoate (4.0 g) were dissolved in THF (30 mL purged with $N_2$) and CuI (0.61 g), Pd(PPh$_3$)$_4$ (1.8 g) and triethylamine (4.1 mL) were added. The mixture was then heated to 100° C. for 6 h, cooled and diluted with EtOAc (10 mL). The solution was washed with 0.2N HCl (2×10 mL), sat. NaHCO$_3$ (2×10 mL) and brine. The organic phase was dried and concentrated by evaporation. The resulting residue was purified by FCC to give the subtitle compound as colourless oil (5.6 g); $^1$H NMR: 7.61 (1H, d), 7.08 (1H, d), 6.99 (1H, dd), 3.80-3.75 (8H, m), 2.63 (2H, t), 0.87 (9H, s), 0.06 (6H, s); ESI m/z 349 (M+1).

(ii) Methyl 4-(4-(tert-butyldimethylsilyloxy)butyl)-2-methoxybenzoate

The product from step (i) (5.6 g) was dissolved in MeOH. 10% Pd/C (50% wet) (1.0 g) was added and the mixture was stirred under $H_2$ for 7 h at r.t. The Pd/C was filtered off and the filtrate was concentrated to give the subtitle compound as colourless oil (5.6 g); $^1$H NMR: 7.56 (1H, d), 6.95 (1H, d), 6.82 (1H, dd), 3.79 (3H, s), 3.74 (3H, s), 3.58 (2H, t), 3.58 (2H, t), 1.64-1.57 (2H, m), 1.50-1.44 (2H, m), 0.83 (9H, s), 0.01 (6H, s); MS:ESI 353 (M+1).

(iii) 4-(4-(tert-Butyldimethylsilyloxy)butyl)-2-methoxyphenyl)methanol

The product from step (ii) (5.6 g) in THF (30 mL) was added to the suspension of LiAlH$_4$ (0.61 g) in THF (50 mL) and the mixture was stirred for 0.5 h at r.t. The mixture was then cooled with an ice-bath and sat. Na$_2$SO$_4$ (2 mL) was added slowly and the mixture was stirred for 2 h at r.t. The mixture was then dried (Na$_2$SO$_4$), precipitate was filtered off using diatomaceous earth (Celite™) and the filtrate was concentrated to give the subtitle compound as colourless oil (4.4 g); $^1$H NMR: 7.22 (1H, d), 6.73-6.71 (2H, m), 4.87 (1H, t), 4.42 (2H, d), 3.73 (3H, s), 3.60-3.56 (2H, m), 2.55 (2H, t,), 1.61-1.57 (2H, m), 1.50-1.43 (2H, m), 0.84 (9H, s), 0.01 (6H, s).

(iv) tert-Butyl(4-(4-(chloromethyl)-3-methoxyphenyl)butoxy)dimethylsilane

Methanesulfonyl chloride (54 µL) was added to the mixture of the product from step (iii) (195 mg) and DIPEA (155 µL) in THF (3 mL) at 0° C. After stirring for 10 mins, LiCl (42 mg) was added and the mixture was stirred for 2 h and then diluted with EtOAc (10 mL). The solution was washed with 0.2N HCl (2×10 mL), sat. NaHCO$_3$ (2×10 mL) and brine. The organic phase was dried and concentrated to give the subtitle compound as colourless oil (200 mg); $^1$H NMR: 7.26 (1H, d), 6.84 (1H, d), 6.74 (1H, dd), 4.65 (2H, s), 3.80 (3H, s), 3.58 (2H, t), 2.57 (2H, t), 1.63-1.58 (2H, m), 1.48-1.34 (2H, m), 0.84 (9H, s), 0.00 (6H, s).

(v) methyl 2-(4-(4-(tert-butyldimethylsilyloxy)butyl)-2-methoxybenzyl)-3-oxobutanoate Methyl acetoacetate (161 L) was added to the suspension of NaH (55% oil dispersion, 43 mg) in THF (5 mL) at 0° C. and the mixture was stirred for 0.5 h. The product from step (iv) (200 mg) in THF (5 mL) and KI (83 mg) were added and the mixture was stirred at 80° C. for 2 h. The mixture was then cooled to r.t. and diluted with EtOAc (30 mL). The mixture was then washed with 0.1N HCl (2×10 mL), sat. NaHCO$_3$ (2×10 mL) and brine. The organic phase was dried and concentrated and the residue was purified by FCC to give the subtitle compound as colourless oil (200 mg); $^1$H NMR: 6.93 (1H, d), 6.76 (1H, d), 6.64 (1H, dd), 3.89-3.85 (1H, m), 3.85 (3H, s), 3.62-3.55 (5H, m), 2.98-2.89 (2H, m), 2.54-2.50 (2H, m), 2.12 (3H, s), 1.59-1.56 (2H, m), 1.46-1.42 (2H, m), 0.84 (9H, s), 0.00 (6H, s); MS:ESI 423 (M+1).

(vi) 2-Amino-5-(4-(4-(tert-butyldimethylsilyloxy)butyl)-2-methoxybenzyl)-6-methylpyrimidin-4-ol Guanidium carbonate (109 mg) was added to a solution of the product from step (v) (200 mg) in MeOH (5 mL) and the mixture was heated at 65° C. for 12 h. The mixture was then cooled to r.t. and diluted with EtOAc (30 mL). The mixture was then washed with sat. NaHCO$_3$ (2×10 mL) and brine. The organic phase was dried and concentrated and the residue was purified by FCC to give the subtitle compound as colourless oil (147 mg); $^1$H NMR: 6.73-6.69 (2H, m), 6.59 (1H, dd), 6.30 (2H, brs), 3.77 (3H, s), 3.57 (2H, t), 3.37 (2H, s), 2.52-2.50 (2H, m), 2.94 (3H, s), 1.59-1.56 (2H, m), 1.46-1.42 (2H, m), 0.84 (9H, s), 0.00 (6H, s).

(vii) 2-Amino-5-(4-(4-(tert-butyldimethylsilyloxy)butyl)-2-methoxybenzyl)-6methylpyrimidin-4-yl 2,4,6-trimethylbenzenesulfonate The subtitle compound was prepared by the method of Example 35 step (v) using the product from step (vi) (142 mg) to give a colourless oil (260 mg); $^1$H NMR: 7.07 (2H, s), 6.75-6.72 (3H, m), 6.61-6.98 (2H, m), 3.72 (3H, s), 3.61-3.57 (4H, m), 2.55-2.51 (2H, m), 2.42 (6H, s), 2.28 (3H, s), 2.24 (3H, s), 1.61-1.54 (2H, m), 1.53-1.42 (2H, m), 0.84 (9H, s), 0.00 (6H, s).

(viii) 5-(4-(4-(tert-Butyldimethylsilyloxy)butyl)-2-methoxybenzyl)-6-methyl-$N^4$ pentylpyrimidine-2,4-diamine The subtitle compound was prepared by the method of Example 36 step (vi) using the product from step (vii) (260 mg) to give a colourless oil (101 mg); $^1$H NMR: 6.78 (1H, s), 6.60 (2H, s), 6.01 (1H, br s), 5.72 (2H, br s), 3.81 (3H, s), 3.58-3.54 (4H, m), 3.25-3.17 (2H, m), 2.53-2.49 (2H, m), 1.96 (3H, s), 1.63-1.51 (2H, m), 1.50-1.37 (4H, m), 1.30-1.08 (4H, m), 0.84-0.78 (12H, m), 0.00 (6H, s); MS:ESI 501 (M+1).

(ix) 4-(4-((2-Amino-4-methyl-6-(pentylamino)pyrimidin-5-yl)methyl)-3methoxyphenyl)butan-1-ol The subtitle compound was prepared by the method of Example 36 step (vii) using the product from step (x) (100 mg) to give a colourless oil (71 mg); $^1$H NMR: 6.79 (1H, s), 6.61-6.50 (2H, m), 5.95 (1H, t), 5.64 (2H, br s), 4.36 (1H, t), 3.82 (3H, s), 3.55 (2H, s), 3.39-3.33 (2H, m), 3.22-3.17 (2H, m), 2.52-2.49 (2H, m), 1.96 (3H, s), 1.57-1.53 (2H, m), 1.42-1.37 (4H, m), 1.22-1.10 (4H, m), 0.80 (3H, t); MS:ESI 387 (M+1).

(x) 5-(4-(4-(Dimethylamino)butyl)-2-methoxybenzyl)-6-methyl-N$^4$-pentylpyrimidine-2,4-diamine The title compound was prepared by the method of Example 37 using the product from step (ix) to give a white solid (58 mg); $^1$H NMR: 6.79 (1H, s), 6.61-6.50 (2H, m), 5.94-5.92 (1H, m), 5.63 (2H, s), 3.82 (3H, s), 3.54 (2H, s), 3.22-3.17 (2H, m), 2.52-2.49 (2H, m), 2.18-2.14 (2H, m), 2.05 (6H, s), 1.95 (3H, s), 1.55-1.49 (2H, m), 1.44-1.32 (4H, m), 1.24-1.09 (4H, m), 0.81 (3H, t); MS:ESI 414 (M+1).

Example 40

(S)-2-(2-Amino-5-(4-(hydroxymethyl)-2-methoxybenzyl)-6-methyl-pyrimidin-4-ylamino)pentan-1-ol (i) (S)-Methyl 4-((2-amino-4-(1-hydroxypentan-2-ylamino)-6-methylpyrimidin-5-yl)-methyl)-3-methoxybenzoate (S)-2-Aminopentan-1-ol (0.481 g) was added to a suspension of the product from Example 12 step (iii) (0.5 g) in dioxane (5 mL) and the mixture was heated in a CEM microwave at 170° C. for 9 h. The mixture was then cooled, the solvent was removed by evaporation. The residue was purified by FCC using 5% MeOH in DCM to give the subtitle compound (0.250 g) as a orange gum; $^1$H NMR: 7.53-7.42 (2H, m), 6.89 (1H, d), 5.75 (2H, d), 5.58 (1H, d), 4.61-4.54 (1H, m), 4.17-4.08 (1H, m), 3.92 (3H, s), 3.83 (3H, s), 3.69 (2H, d), 3.28-3.23 (m, 1H), 2.00 (3H, d), 1.53-1.40 (m, 1H), 1.35-1.19 (m, 2H), 1.16-1.02 (m, 2H), 0.77 (3H, t); LC-MS m/z 389.

(ii) (S)-4-((2-Amino-4-(1-hydroxypentan-2-ylamino)-6-methylpyrimidin-5-yl)methyl)-3-methoxybenzoic acid The product from step (i) (220 mg) was dissolved in THF (3 mL) and water (3 mL) and LiOH solution (3M, 0.944 mL) was then added. The mixture was then heated in a CEM microwave for 6 h at 120° C. The solvent was then removed by evaporation and the resulting residue was dissolved in water and acidified with 2 M HCl to pH7. The resulting solid precipitate was filtered off and dried under high vacuum overnight to give subtitle compound (90 mg); $^1$H NMR: 7.53-7.42 (2H, m), 6.92 (1H, d), 6.61 (2H, d), 4.21 (1H, d), 3.91 (3H, d), 3.75 (2H, s), 2.09 (3H, s), 1.53-1.42 (1H, m), 1.40-1.20 (2H, m), 1.09 (2H, q), 0.78 (3H, t); LC-MS m/z 375.

(iii) (S)-2-(2-Amino-5-(4-(hydroxymethyl)-2-methoxybenzyl)-6-methylpyrimidin-4-ylamino)pentan-1-ol Borane-THF complex (1M, 3 mL, 3.00 mmol) was added to the product of step (ii) (85 mg) and the mixture was heated to 80° C. for 2 h. MeOH was then carefully added and the mixture was heated to 80° C. for 1 h. The solvent was then removed by evaporation and the resulting residue was dissolved in MeOH and loaded onto a SCX cartridge. The cartridge was washed with MeOH and eluted with a solution of 0.7M NH$_3$ in MeOH. The solvents were evaporated to give title compound as a colourless gum (40 mg); $^1$H NMR: 6.94 (1H, s), 6.74 (2H, q), 5.66 (2H, s), 5.48 (1H, t), 5.14 (1H, s), 4.59 (1H, s), 4.45 (2H, s), 4.15-4.04 (1H, m), 3.84 (3H, d), 3.59 (2H, d), 3.25 (1H, dd), 2.03 (3H, s), 1.54-1.44 (1H, m), 1.32-1.23 (2H, m), 1.11 (2H, m), 0.81-0.76 (3H, t); LC-MS m/z 361.

The invention claimed is:
1. A compound of Formula (I), or a pharmaceutically acceptable salt thereof:

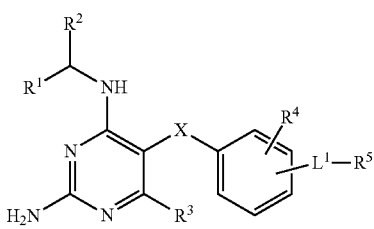

(I)

wherein:
X represents —CH$_2$—, —NR$^8$—, —O— or —S(O)$_n$—;
R$^1$ represents C$_{1-6}$alkyl, C$_{2-6}$alkoxy, C$_{1-6}$alkoxyC$_{1-6}$alkyl, hydroxyC$_{1-6}$alkyl, hydroxyC$_{1-6}$alkoxy or hydroxyC$_{1-6}$alkoxyC$_{1-6}$alkyl;
R$^2$ represents hydrogen, C$_{1-6}$alkyl or phenyl wherein said phenyl is optionally substituted with 1, 2 or 3 substituents selected from R$^6$;
R$^3$ represents C$_{1-6}$alkyl, C$_{1-6}$alkoxy or —S—C$_{1-6}$alkyl;
R$^4$ represents hydrogen, halogen, C$_{1-6}$alkyl or C$_{1-6}$alkoxy;
L$^1$ represents a direct bond, —(CR$^9$R$^{10}$)$_m$—, —CH=CH—(CR$^9$R$^{10}$)$_q$—, —C≡C—(CR$^9$R$^{10}$)$_q$—, —O—(CR$^9$R$^{10}$)$_q$—, —C(O)—O—(CR$^9$R$^{10}$)$_q$— or —O—(CH$_2$)$_q$—NR—(CH$_2$)$_q$—;
R$^5$ represents —NR$^{11}$R$^{12}$, C$_{3-6}$cycloalkyl, phenyl or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from R$^7$;
R$^6$ represents C$_{1-6}$alkyl, fluoroC$_{1-6}$alkyl, C$_{1-6}$alkoxy, hydroxy, halogen, cyano, —S(O)$_n$—C$_{1-6}$alkyl or —CH$_2$—C(O)—O—C$_{1-6}$alkyl;
R$^7$ represents C$_{1-6}$alkyl, C$_{1-6}$alkoxy, C$_{1-6}$alkoxyC$_{1-6}$alkyl, hydroxy, hydroxyC$_{1-6}$alkyl or —(CH$_2$)$_q$—NR$^{11}$R$^{12}$;
R$^8$ represents hydrogen or C$_{1-6}$alkyl;
R$^9$ and R$^{10}$ independently represent hydrogen or methyl;
R$^{11}$ and R$^{12}$ independently represent hydrogen, C$_{1-4}$alkyl or C$_{1-4}$alkoxyC$_{2-4}$alkyl;
m represents 1, 2, 3, 4, 5 or 6;
n represents 0, 1 or 2; and
q represents 0, 1, 2, 3, 4, 5 or 6.

2. A compound according to claim 1, or a pharmaceutically acceptable salt thereof, wherein X represents —CH$_2$—.

3. A compound according to claim 1, or a pharmaceutically acceptable salt thereof, wherein R$^1$ represents C$_{1-6}$alkyl.

4. A compound according to claim 1, or a pharmaceutically acceptable salt thereof, wherein $R^2$ represents hydrogen.

5. A compound according to claim 1, or a pharmaceutically acceptable salt thereof, wherein $R^2$ represents phenyl wherein said phenyl is optionally substituted with 1, 2 or 3 substituents selected from $R^6$.

6. A compound according to claim 1, or a pharmaceutically acceptable salt thereof, wherein $R^3$ represents methyl.

7. A compound according to claim 1, or a pharmaceutically acceptable salt thereof, wherein $R^4$ represents $C_{1-6}$alkoxy.

8. A compound according to claim 1, or a pharmaceutically acceptable salt thereof, wherein $R^4$ represents hydrogen.

9. A compound according to claim 1, or a pharmaceutically acceptable salt thereof, wherein $R^4$ is bonded at the ortho position of the phenyl ring relative to linkage —X—.

10. A compound according to claim 1, or a pharmaceutically acceptable salt thereof, wherein q represents 1, 2 or 3.

11. A compound according to claim 1, or a pharmaceutically acceptable salt thereof, wherein q represents 2 or 3.

12. A compound according to claim 1, or a pharmaceutically acceptable salt thereof, wherein $L^1$ represents —$(CR^9R^{10})_m$—, —CH=CH—$(CR^9R^{10})_q$— or —C≡C—$(CR^9R^{10})_q$—.

13. A compound according to claim 1, or a pharmaceutically acceptable salt thereof, wherein $L^1$ represents —O—$(CR^9R^{10})_q$—.

14. A compound according to claim 1, or a pharmaceutically acceptable salt thereof, wherein $L^1$ is bonded at the para position of the phenyl ring relative to linkage —X—.

15. A compound according to claim 1, or a pharmaceutically acceptable salt thereof, wherein $L^1$ is bonded at the meta position of the phenyl ring relative to linkage —X—.

16. A compound according to claim 1, or a pharmaceutically acceptable salt thereof, wherein $L^1$ is bonded at the ortho position of the phenyl ring relative to linkage —X—.

17. A compound according to claim 1, or a pharmaceutically acceptable salt thereof, wherein $R^5$ represents $NR^{11}R^{12}$ or a monocyclic 4, 5, 6 or 7 membered heterocyclic ring which comprises 1, 2 or 3 heteroatoms independently selected from O, N or S wherein said heterocyclic ring is optionally substituted with 1, 2 or 3 substituents selected from $R^7$.

18. A compound according to claim 1, or a pharmaceutically acceptable salt thereof, wherein $R^5$ represents $NR^{11}R^{12}$ and $R^{11}$ and $R^{12}$ both represent methyl.

19. A pharmaceutical composition which comprises a compound according to any one of claims 1 to 18, or a pharmaceutically acceptable salt thereof, in association with a pharmaceutically acceptable diluent or carrier.

20. A compound according to claim 1, or a pharmaceutically acceptable salt thereof, wherein $R^5$ represents —$NR^{11}R^{12}$, $C_{3-6}$ cycloalkyl, phenyl or a monocyclic 4, 5, 6 or 7 membered heterocyclic ring which comprises 1, 2 or 3 heteroatoms independently selected from O, N or S wherein said phenyl and heterocyclic rings are optionally substituted with 1, 2 or 3 substituents selected from $R^7$.

21. A compound according to claim 12, or a pharmaceutically acceptable salt thereof, wherein $R^5$ represents $NR^{11}R^{12}$ or a monocyclic 4, 5, 6 or 7 membered heterocyclic ring which comprises 1, 2 or 3 heteroatoms independently selected from O, N or S wherein said heterocyclic ring is optionally substituted with 1, 2 or 3 substituents selected from $R^7$.

22. A compound according to claim 13, or a pharmaceutically acceptable salt thereof, wherein $R^5$ represents $NR^{11}R^{12}$ or a monocyclic 4, 5, 6 or 7 membered heterocyclic ring which comprises 1, 2 or 3 heteroatoms independently selected from O, N or S wherein said heterocyclic ring is optionally substituted with 1, 2 or 3 substituents selected from $R^7$.

23. A compound according to claim 1, or a pharmaceutically acceptable salt, wherein the compound is:
- 5-(4-(2-(Dimethylamino)ethoxy)benzyl)-6-methyl-$N^4$-pentylpyrimidine-2,4-diamine;
- 5-(4-(3-(Dimethylamino)propoxy)benzyl)-6-methyl-$N^4$-pentylpyrimidine-2,4-diamine;
- 6-Methyl-$N^4$-pentyl-5-(4-(2-(piperidin-1-yl)ethoxy)benzyl)pyrimidine-2,4-diamine;
- 6-Methyl-$N^4$-pentyl-5-(4-(2-(pyrrolidin-1-yl)ethoxy)benzyl)pyrimidine-2,4-diamine;
- 5-(4-(2-(Benzyl(methyl)amino)ethoxy)benzyl)-6-methyl-$N^4$-pentyl-pyrimidine-2,4-diamine;
- 6-Methyl-$N^4$-pentyl-5-(4-(3-(pyrrolidin-1-yl)propoxy)benzyl)pyrimidine-2,4-diamine;
- 6-Methyl-5-(4-(3-(4-methylpiperazin-1-yl)propoxy)benzyl)-$N^4$-pentylpyrimidine-2,4-diamine;
- 5-(4-(3-(Dimethylamino)propoxy)-2-methoxybenzyl)-6-methyl-$N^4$-pentylpyrimidine-2,4-diamine;
- (S)-4-(Dimethylamino)butyl 4-((2-amino-4-(1-hydroxypentan-2-yl-amino)-6-methylpyrimidin-5-yl)methyl)-3-methoxybenzoate;
- 5-(2-(3-(Dimethylamino)propoxy)benzyl)-6-methyl-$N^4$-pentyl-pyrimidine-2,4-diamine;
- 5-(3-(3-(Dimethylamino)propoxy)benzyl)-6-methyl-$N^4$-pentyl-pyrimidine-2,4-diamine;
- 6-Methyl-$N^4$-pentyl-5-(3-(2-(piperidin-1-yl)ethoxy)benzyl)pyrimidine-2,4-diamine;
- 5-(3-(2-(Dimethylamino)ethoxy)benzyl)-6-methyl-$N^4$-pentylpyrimidine-2,4-diamine;
- 6-Methyl-$N^4$-pentyl-5-(3-(2-(pyrrolidin-1-yl)ethoxy)benzyl)pyrimidine-2,4-diamine;
- 5-(3-((Dimethylamino)methyl)benzyl)-6-methyl-$N^4$-pentylpyrimidine-2,4-diamine;
- 5-(4-(3-(Dimethylamino)prop-1-ynyl)benzyl)-6-methyl-$N^4$-pentyl-pyrimidine-2,4-diamine;
- 5-(4-(3-(Dimethylamino)propyl)benzyl)-6-methyl-$N^4$-pentylpyrimidine-2,4-diamine;
- 5-(3-(3-(Dimethylamino)propyl)benzyl)-6-methyl-$N^4$-pentylpyrimidine-2,4-diamine;
- 5-(4-(3-(Dimethylamino)propoxy)-2-methylbenzyl)-6-methyl- $N^4$-pentylpyrimidine-2,4-diamine;
- (R)-Methyl2-(3-(1-(2-amino-5-(4-(3-(dimethylamino)propoxy)-2-methoxybenzyl)-6-methylpyrimidin-4-ylamino)-3-hydroxypropyl)phenyl)acetate;
- 5-(2-Methoxy-4-(3-morpholinopropoxy)benzyl)-6-methyl- $N^4$-pentylpyrimidine-2,4-diamine;
- 5-(2-Methoxy-4-(3-(4-methylpiperazin-1-yl)propoxy)benzyl)-6-methyl- $N^4$-pentylpyrimidine-2,4-diamine; or
- 5-(4-(4-(Dimethylamino)butyl)-2-methoxybenzyl)-6-methyl-$N^4$-pentylpyrimidine-2,4-diamine.

24. A pharmaceutical composition comprising a compound according to claim 23, or a pharmaceutically acceptable salt thereof, in association with a pharmaceutically acceptable diluent or carrier.

* * * * *

UNITED STATES PATENT AND TRADEMARK OFFICE
CERTIFICATE OF CORRECTION

PATENT NO. : 9,533,978 B2  
APPLICATION NO. : 14/469515  
DATED : January 3, 2017  
INVENTOR(S) : Nicholas James Bennett et al.

Page 1 of 1

It is certified that error appears in the above-identified patent and that said Letters Patent is hereby corrected as shown below:

On the Title Page

Item (71), in the Applicant:
"AstraZeneca AB, Sodertalje (SE)" should read -- Sumitomo Dainippon Pharma Co., Ltd., Osaka (JP) --.

In the Claims

In Claim 1, Column 54, Line 43:
"–O–(CH$_2$)$_q$–NR–(CH$_2$)$_q$–;" should read -- –O–(CH$_2$)$_q$–NR$^8$–(CH$_2$)$_q$–; --.

Signed and Sealed this  
Twelfth Day of September, 2017

Joseph Matal  
*Performing the Functions and Duties of the  
Under Secretary of Commerce for Intellectual Property and  
Director of the United States Patent and Trademark Office*